United States Patent
Morozov et al.

(10) Patent No.: US 7,960,184 B2
(45) Date of Patent: Jun. 14, 2011

(54) METHODS AND DEVICES FOR ACTIVE BIOASSAY

(75) Inventors: Victor Morozov, Manassas, VA (US); Tamara Morozova, Manassas, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 1223 days.

(21) Appl. No.: 10/665,722

(22) Filed: Sep. 19, 2003

(65) Prior Publication Data

US 2004/0115709 A1 Jun. 17, 2004

Related U.S. Application Data

(60) Provisional application No. 60/412,664, filed on Sep. 20, 2002.

(51) Int. Cl.
G01N 27/00 (2006.01)
G01N 33/00 (2006.01)
G01N 33/48 (2006.01)
G01N 33/50 (2006.01)
G01N 33/543 (2006.01)
G01N 33/553 (2006.01)

(52) U.S. Cl. ......... 436/526; 422/68.1; 422/81; 422/101; 422/102; 422/103; 422/104; 435/4; 435/287.2; 435/287.3; 435/288.5; 436/149; 436/150; 436/523

(58) Field of Classification Search .................. 422/68.1, 422/81, 101, 102–104; 435/4, 287.2, 287.3, 435/288.5; 436/149, 150, 523
See application file for complete search history.

(56) References Cited

U.S. PATENT DOCUMENTS

| | | | | |
|---|---|---|---|---|
| 4,040,940 A | * | 8/1977 | Bier | 204/601 |
| 4,584,075 A | * | 4/1986 | Goldstein et al. | 204/522 |
| 4,889,606 A | * | 12/1989 | Dyson et al. | 204/464 |
| 5,028,657 A | * | 7/1991 | Hsu et al. | 525/54.1 |
| 5,290,825 A | * | 3/1994 | Lazar | 523/176 |

(Continued)

FOREIGN PATENT DOCUMENTS

JP 63315115 A * 12/1988

OTHER PUBLICATIONS

Avseenko, N.V., et al. "Immunoassay with Multicomponent Protein Microarrays Fabricated by Electrospray Deposition", *Analytical Chemistry*, vol. 74, 927-933, 2002.

(Continued)

*Primary Examiner* — Unsu Jung
(74) *Attorney, Agent, or Firm* — David Yee; Edgar Rodriquez; David Grossman

(57) ABSTRACT

The present invention provides an active assay method for detecting a biological analyte. According to the method, a probe molecule is immobilized on a surface. An analyte is then placed in fluidic connection with the probe molecule on the surface. A force is then applied to the analyte to move it toward the surface to facilitate contact and possibly binding of the analyte to the probe. Optionally, another force can be applied or the force can be reversed, to remove unbound or weakly bound analyte from the surface. Analyte that remains bound to the surface is then detected. The detection can include rolling or sliding beads over an analyte and/or probe on a substrate, and detecting bound beads. The present invention furthermore, provides devices, such as electrophoresis apparatuses and biochip assemblies, for carrying out the methods of the invention.

27 Claims, 15 Drawing Sheets

U.S. PATENT DOCUMENTS

| | | | |
|---|---|---|---|
| 5,865,766 A | | 2/1999 | Bonsall et al. |
| 5,876,753 A | * | 3/1999 | Timmons et al. ............. 427/488 |
| 5,981,297 A | * | 11/1999 | Baselt ........................... 436/514 |
| 6,037,186 A | * | 3/2000 | Stimpson ...................... 436/518 |
| 6,045,676 A | | 4/2000 | Mathies et al. |
| 6,082,555 A | * | 7/2000 | Fane ............................... 211/50 |
| 6,133,043 A | * | 10/2000 | Talley et al. .................. 436/172 |
| 6,245,508 B1 | * | 6/2001 | Heller et al. ....................... 435/6 |
| 6,267,858 B1 | * | 7/2001 | Parce et al. .................... 204/600 |
| 6,309,875 B1 | * | 10/2001 | Gordon ...................... 435/287.2 |
| 6,329,209 B1 | * | 12/2001 | Wagner et al. .................. 506/13 |
| 6,350,609 B1 | | 2/2002 | Morozov et al. |
| 6,406,921 B1 | * | 6/2002 | Wagner et al. ................ 436/518 |
| 2001/0045359 A1 | * | 11/2001 | Cheng et al. .................. 204/547 |
| 2002/0001803 A1 | * | 1/2002 | Smith et al. ........................ 435/6 |
| 2002/0095073 A1 | * | 7/2002 | Jacobs et al. .................. 600/300 |
| 2003/0146100 A1 | * | 8/2003 | Huang et al. .................. 204/547 |

OTHER PUBLICATIONS

Avseenko, N.V., et al., "Immobilization of proteins in Immunochemical Microarrays Fabricated by Electrospray Deposition", *Analytical Chemistry*, vol. 73, 6047-6052, 2001.

Baselt, D.R. et al., "A biosensor based on magnetoresistance technology," *Biosensors & Bioelectronics*, vol. 13, 731-739, 1998.

Kritz, K. et al., "Advancements toward magneto assay" *Biosensors & Bioelectronics*, vol. 13, 817-823, 1998.

Lee, G.U. et al., "Implementation of force Differentiation in the Immunoassay", *Analytical Biochemistry*, vol. 287, 261-271, 2000.

Morozov V.N. and Morozova T.Ya., "Mechanical Detection of Interaction of Small Specific Ligands with Proteins and DNA in Cross-Linked Samples", *Analytical Biochemistry*, vol. 201, 68-79, 1992.

Morozov V.N. et al. "New polyacrylamide gel-based method of sample preparation for optical microscopy: Immobilization of DNA molecules for optical mapping" *Journal Microscopy*, vol. 183, 205-214, 1996.

Morozov, V.N. and Morozova, T.Ya., "Electrospray deposition as a method for mass fabrication of mono- and multi-component microarrays of biological and biologically active substances", *Analytical Chemistry*, vol. 71, 3110-3117, 1999.

Yamagata, Y,. et al., "A Device for Testing Protein-Ligand Interaction using Mechano-Chemical Effect", *ASME Bioengineering Conference*, BED-vol. 50, pp. 175-176, 2001.

* cited by examiner

METHODS AND DEVICES FOR ACTIVE BIOASSAY

RELATED APPLICATION DATA

This application claims the benefit of priority under 35 U.S.C. §119(e) of U.S. Ser. No. 60/412,664, filed Sep. 20, 2002, the entire content of which is incorporated herein by reference.

BACKGROUND OF THE INVENTION

1. Field of the Invention

The invention relates generally to assay methods for detection of biological molecules, viruses, and cells, and more specifically to solid-phase assay methods for detection of biological molecules, viruses, and cells in solution, based on active motion of analytes to and from probe molecules under action of electrostatic, magnetic, centrifugal (gravitation) or hydrodynamic forces.

2. Background Information

There are several principal limits in conventional bioassay methods: (i) diffusion limit for transport of analyte to immobilized probes, (ii) limits for the assay sensitivity due to limited affinity of probe molecules and, (iii) limits for the assay sensitivity due to unspecific binding of analyte molecules with surface, which we will further refer to as a background limit.

Diffusion Limit

In most practical cases of heterogeneous analysis assay time is limited by the diffusion of analyte molecules to the surface with immobilized probes. The problem was carefully analyzed upon development of the BIAcore plasmon resonance technique (Nieba et al., 1996; Myszka et al., 1998).

As an example, let us consider that probe molecules are immobilized on a substrate in a mono-layer with a surface density of $C_s$ molecules per unit area. Let us also assume that probe molecules have infinitely large affinity with respect to the analyte molecules, so, that every molecule touching the surface binds to a probe molecule. Under these conditions time needed to saturate half of the probes on the surface will be described by the equation (Morozov & Morozova, (1992)):

$$\tau_{1/2} \approx C_s \delta / C_o D \quad (1)$$

$\delta$ is the thickness of unstirred layer, D is the diffusion coefficient, $C_o$ is the analyte concentration in solution. The thickness of unstirred layer depends on the flow rate of liquid, V, and on the size of the surface, according to the following equation (Tunizkii, (1970)):

$$\delta = (vb/V)^{1/2}(D/v)^{1/3} \quad (2)$$

with v denoting the kinematic viscosity of liquid, and b denoting a characteristic size of the sensor element. Since the diffusion coefficient can only slightly be decreased by raising temperature the only way to enhance the diffusion-controlled reaction in such a passive heterogeneous system is to decrease the thickness of the unstirred layer. Intensive shaking of micro-titer plates, pressing solution through a narrow slot in the BIAcore apparatus are examples of solving the transport problem. However, these approaches cannot solve the problem completely: as seen from the Eqn. (2) the thickness of unstirred layer depends weakly on the flow rate. Thus, 100-fold increase in the rate of solution flow will accelerate the reaction only 10 times.

As an example, let us consider a sensor with the size of 5×5 mm² (b=5 mm) in a flow of analyte solution, V=5 cm/sec. For protein analyte molecules with the diffusion coefficient, $D=5 \times 10^{-10}$ m²/cek, moving in a water solution with viscosity, $v=1 \times 10^{-6}$ m²/sec, $\delta=(vb/V)^{1/2}(D/v)^{1/3}=25$ µm. Assuming that sensor surface is covered by a monolayer of probe molecules, d=5 nm in diameter we estimate the density of probe molecules as $C_s=1/N_a d^2$. $N_a$ denotes the Avogadro number. Time needed to saturate half of all the probe from a solution with concentration, $C_o$, can then be estimated as $\tau_{1/2}=C_s \delta / 2C_o D=1.7 \times 10^6/C_o$. Thus, even under such ideal conditions diffusion will limit the assay time of analyte solution with $C_o=1$ nM to about 0.5 h. Therefore, there remains a need for methods for performing bioassays that decrease the time for performing the assay.

Affinity Limit.

In contrast to the assumption made in the example discussed above the real probe molecules (e.g., antibodies) in any practical system have a limited affinity, characterized by a dissociation constant, $K_d$, which is the ratio of the backward, $k_{diss}$, and the forward reaction rate, $k_{ass}$, as:

$$K_d = k_{diss}/k_{ass} \quad (3)$$

Fraction of probe molecules, (AP)/P, occupied by analyte molecules bound at equilibrium from a solution with concentration, $C_o$, is described by the equation:

$$(AP)/P = C_o/(C_o + K_d) \quad (4)$$

Thus, to have half of the probe molecules occupied with the analyte its concentration in solution should be equal to $K_d$. Dissociation constants of antibodies vary between $10^{-7}$ M and $10^{-10}$ M and often present a limit for assay sensitivity.

Background Limit.

Background in bioassay often results from a weak unspecific interaction of analyte molecules with substrate. Though blocking the surface with proteins (BSA, dry milk and casein in immunoassay) and grafting inert polymers to surface (Chapman et al., 2000) considerably reduce the background, they never remove it completely. A radical method to reduce the background was suggested by Lee et al., (2000). They suggested applying a weak force to mechanically detach weakly bound analyte molecules from the surface. Since forces they applied were not enough to destroy specific interactions, only beads bound to the substrate surface via strong specific interactions remained. Therefore, there remains a need for methods for performing bioassays that provide reduced backgrounds.

SUMMARY OF THE INVENTION

The present invention provide methods and devices that overcome the diffusion, affinity, and background limitations of the prior art, by providing methods and devices for performing active bioassays. Methods and procedures for active bioassay employ different external forces to actively transport analyte molecules to and from probe molecules immobilized on a solid support. Different aspects of the method exploit electric, magnetic, enhanced gravitational and hydrodynamic forces.

The methods of the present invention have several advantages over standard assays controlled by diffusion: (i) the methods can be performed in seconds and minutes, rather than in hours, (ii) the methods provide reduction in background using active washing as a means to discriminate between specifically and non-specifically bound ligands, and (iii) the methods increase bioassay sensitivity by concentrating analyte molecules in the vicinity of probe molecules. It is also illustrated herein, that the active assay methods and procedures of the present invention are especially advantageous when combined with microarrays of probe molecules. This combination allows multiple assays to be performed in a short period of time.

In one embodiment, the present invention provides a method for detecting a biological molecule. According to the method, a probe is immobilized on a surface. An analyte is then placed in fluidic connection with the probe molecule on the surface. For example, the surface with the immobilized probe molecule can be placed in a channel, wherein the channel comprises an analyte solution or suspension. A force is then applied to the analyte to move it toward the surface to facilitate contact and possibly binding of the analyte to the probe. Optionally, another force can be applied or the force can be reversed, to remove unbound or weakly bound analyte from the surface. Analyte that remains bound to the surface is then detected.

In illustrative examples, the surface is modified to facilitate binding of the probe to the surface. In these illustrative example, the method typically further includes adsorbing or covalently binding the probe molecule to the surface.

In certain aspects, the present invention provides electrophoretically enhanced ELISA, wherein antigens are immobilized onto a dialysis membrane and a transverse electric field is applied to transport charged primary and secondary antibodies to and from the membrane. In another aspect, the present invention provides isotachophoresis to move and concentrate analyte molecules in the vicinity of probe molecules. In yet another aspect, the present invention provides a method wherein analyte molecules are transported to and from a membrane, using beads as vehicles and external gravitational (centrifugal) and magnetic forces as a means to control motion of the beads. In yet another aspect, the present invention provides a method wherein probe molecules are deposited as arrays and a combination of electric, centrifugal and magnetic forces is used to control motion of different components of sandwich bioassay. In yet another aspect, the present invention provides a method wherein analyte molecules, whole cells or cell fragments are actively deposited and captured on membrane surfaces and actively probed by rolling beads covered with specific antibodies against the bound species. One aspect of this active procedure includes electro-concentration of analyte on beads, covered with capturing antibodies with subsequent sorting of beads with bound analytes on a microarray of antibodies.

In another embodiment, the present invention provides an apparatus or device for performing an active assay method of the present invention, for example active electrophoresis. The apparatus includes the following:

an upper (10) and a lower electrode chamber (20);
an electrode system (30 (upper) and 40 (lower)) disposed in the upper (10) and lower (20) electrode chamber;
a plurality of channels (60), for example formed using a multi-well microplate (50), having a semi-permeable bottom through which travels electrical current provided by the electrode system (30, 40);
a multi-socket connector (70) matching the wells of the microplate (50); and
and optionally, a deflector (80) disposed in the lower electrode chamber (20), wherein the deflector (80) is effective for deflecting away from the bottom of the channels, gaseous electrochemical products that form in the lower electrode chamber (80).

In another embodiment, the present invention provides an assembly for performing an electrophoretically-assisted assay. The assembly includes the following:

an upper and a lower electrode chamber;
an electrode system disposed in the upper and lower electrode chamber,
a plurality of channels through which an electrical current generated by the electrode system passes; and
a plurality of semi-permeable membranes each having an activated surface, wherein the semi-permeable membranes are positioned across the channels such that current passing through the plurality of channels, passes through the plurality of semi-permeable membranes, and wherein the semi-permeable membranes are penetrable for salt and buffer ions, but not for protein or polynucleotide analytes.

In certain aspects, the assembly includes a deflector disposed in the lower electrode chamber, wherein the deflector is effective for deflecting away from the bottom of the channels, gaseous electrochemical products that form in the lower electrode chamber. In certain aspects, an array of probe molecules is bound to each semi-permeable surface.

In another embodiment, the present invention provides a plate for an active assay. The plate includes a plurality of channels and a plurality of semi-permeable surfaces with activated surfaces positioned across the channels, wherein each membrane of the plurality of semi-permeable membranes is positioned across a channel of the plurality of channels.

In certain aspects, a probe or a plurality of probes, is bound to the surface of the semi-permeable membrane. The plurality of probes, for example can be an array of probes that are bound to each surface of the plurality of semi-permeable membranes. In certain examples, the analyte is a protein or a nucleic acid.

DETAILED DESCRIPTION OF THE INVENTION

Figure 1:
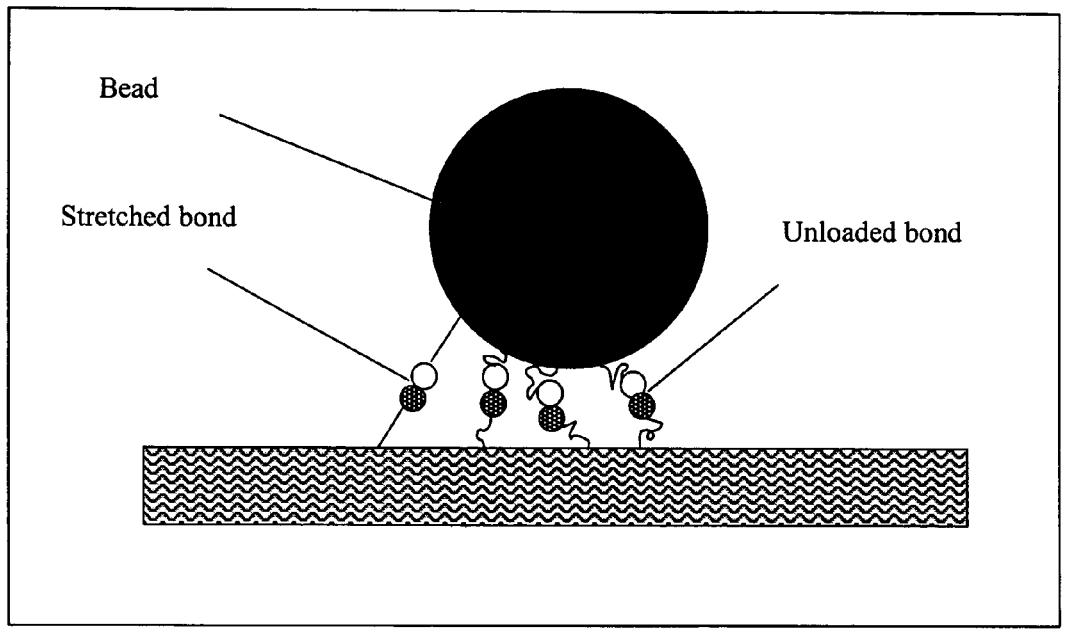
FIG. 1 provides a schematic of multiple bond between a functionalized bead and surface with immobilized probes FIG. 2 provides a schematic of a device used for electrophoretic acceleration of ELISA in separate cells. The device was also used in microarray-based ELISA and in immunoassay with bead detection.

In general, the present invention provides methods whereby analyte molecules are delivered and concentrated in vicinity of immobilized probes by application of electric, magnetic, centrifugal (gravitational) or hydrodynamic force, or a combination thereof. As indicated above, replacement of diffusion with active transport results both in acceleration of the assay and in increased assay sensitivity.

In one embodiment, the present invention provides a method for performing an active biological assay. According to the method, a first binding pair member and a second binding pair member are provided in a reaction chamber. A first force is applied to the first binding pair member, thereby moving it toward the second binding pair member and allowing the formation of a complex that includes the first binding pair member and the second binding pair member. A second force, or a reversed first force, is then applied to detach the first binding pair member from the second binding pair member, if the association between the first and second binding pair members is weak. The force transfers the weakly bound first binding pair member away from the second binding pair member. A first binding pair member that remains bound to the second binding pair member after the force is applied, is then detected.

Typically, the second binding pair member is held in a relatively stationary position from a macroscopic perspective, for example bound to a surface, while the first force is applied, so that the first force can bring the first binding pair member into close enough proximity to the second binding pair member, to facility binding of the first binding pair member to the second binding pair member, if they are members of the same binding pair.

In certain aspects of the invention, the first binding pair member is concentrated near the second binding pair member in the reaction chamber. As indicated below, methods of the present invention in certain aspects, use active transport to accumulate reagents, such as a first binding pair member, typically an analyte, near the second binding pair member, typically a probe, to increase the local concentration of the analyte near the probe, which increases the sensitivity of the methods of the present invention, as discussed in more detail herein.

The methods of the present invention are beneficial, for example, for clinical analysis, diagnostics, and monitoring biohazards in the environment.

The first binding pair member, for example, is an analyte, such as an analyte in a biological sample. The second binding member, for example, is a biological probe, such as an antibody.

Accordingly, in a related embodiment, the present invention provides a method for detecting a biological molecule. According to the method, a probe molecule is immobilized on a surface. An analyte is then placed in fluidic connection with the probe molecule on the surface. For example, the surface with the immobilized probe molecule can be placed in a channel, wherein the channel comprises an analyte solution or suspension. A force is then applied to the analyte to move it toward the surface to facilitate contact and possibly binding of the analyte to the probe. Optionally, another force can be applied or the force can be reversed, to remove unbound or weakly bound analyte from the surface. Analyte that remains bound to the surface is then detected.

In illustrative examples, the surface is modified to facilitate binding of the probe to the surface. In these illustrative example, the method typically further includes adsorbing or covalently binding the probe molecule to the surface. The modification is referred to herein as activation. Thus, if the surface of a membrane is modified, an activated membrane is formed. Specific examples of methods for activating the surface of a membrane are provided in Example 6. One embodiment of the present invention provides a method for activating a membrane with respect to binding of a biological probe by modifying a surface layer of the membrane using plasma discharge. Cold plasma affects only the top 10 nm depth surface layer on a membrane surface (Martinez, A. J., et al., (2000)) and introduces a rich variety of chemical groups (carbonyl, carboxyl, peroxide and other groups, for oxygen or water plasma) (Nuzzo & Smolinsky (1984); Clement, F., et al., (2002)), which can be used to bind protein and other probe molecules. The Examples provided herein illustrate a specific method for activating a dialysis membrane.

In another embodiment, the present invention provides a method for activating a membrane by hydrophobization. As illustrated in the examples, hydrophobization of the membrane surface results in a drastic increase in protein binding. For example, hydrophobization can be achieved either by deposition of octyl cyanoacrylate vapor or by a treatment with silanes without sacrificing membrane ability to support ionic current. A plasma-treated surface of a dialysis membrane can be rapidly made hydrophobic by keeping the membrane in a vapor of dichlorodimethylsilane (DDS). Since this reagent is sensitive to water the procedure is typically performed in atmosphere of dry nitrogen. For example, as illustrated in the Examples, a membrane can be placed for 5-15 min into ajar where a flow of nitrogen passed through a vial with DDS was introduced. The Examples provide details regarding a variety of other techniques for membrane surface activation, such as activation of carboxyl and aldehyde (ketone) groups, for example, by treatment with EDC and NHS, or binding of oxidized dextran linker to a plasma-treated surface using adipic acid dihydrazide.

In certain aspects of the invention, for example those using electrophoretic forces, the surface is a surface of a semi-permeable membrane, penetrable for salt and buffer ions, but not for analytes. A membrane is not penetrable for an analyte when an analyte will not penetrate below 100 angstroms from the surface.

A semi-permeable membrane can be any of a wide variety of membranes known in the art that are capable of binding a binding pair member such as an analyte or a probe. Semi-permeable membranes are available, for example, from Millipore Corp. (Billerica, Mass.) and Spectrum Laboratories, Inc. In one aspect, more than one, for example two, semi-permeable membrane are used, one of which contains probes bound to its surface.

Certain activated membranes that are particularly well-suite for the methods and devices of the present invention, provide another embodiment of the invention. In one aspect the activated membrane (i.e. a membrane that includes a surface layer of at least 5, 10, 25, 50, 100, 250, 500, or 1000 nm, as non-limiting examples, that can adsorb or covalently bind an analyte) is a membrane that is penetrable to salt and buffer ions, but not penetrable to an analyte. In certain aspects, the membrane is transparent. For example, for protein or nucleic acid analytes, the membrane can be a transparent ultrafiltration membrane that has been activated for adsorption of proteins and/or nucleic acids. On the other hand, where the analyte is a whole cell or virus, a microfiltration membrane of appropriate pore size can be used.

In certain examples, the surface layer is a layer of biologically inert polymer used as a linker, typically a grafted polymer, for example dextran or polyethylene oxide. In certain examples, the polymer layer can be 100 nm, 250 mm. 500 nm, or 1 µm.

The membrane in certain illustrative examples is prepared from regenerated cellulose (Sigma, Fisher, Spectrum laboratories, Inc). Membranes prepared from regenerated cellulose are well-suited for the inventions disclosed herein because of their optical transparency and a mechanical strength. In one example, the membrane is a dialysis membrane. The regenerated cellulose membrane is activated using methods provided herein, for example to facilitate adsorption of proteins or nucleic acids.

In certain aspects, the surface is an active surface layer that is separable from the semi-permeable membrane. For example, the surface can be a separable layer formed of particles functionalized with the probe. A wide variety of particles have been disclosed for use in biological assays, as disclosed below in further detail, virtually any of which can be used for certain aspects of the present invention. In certain illustrative examples, the particles are magnetic particles, as are known in the art and illustrated in Example 7.

Particles used in the methods of the present invention are typically at least about 20 nm and not more than about 20 microns, usually at least about 40 nm and less than about 10 microns. The particles may be organic or inorganic, swellable or non-swellable, porous or non-porous, and preferably suspendable in water. The particles may or may not have a charge. The particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may be latex particles or other particles comprised of organic or inorganic polymers; lipid bilayers, e.g., liposomes, phospholipid vesicles; oil droplets; silicon particles; metal sols; cells; and dye crystallites.

The organic particles will normally be polymers, either addition or condensation polymers, which are readily dispersible in the assay medium. The organic particles will also be adsorptive or functionalizable so as to bind at their surface, either directly or indirectly, an sbp member.

The particles can be derived from naturally occurring materials, naturally occurring materials which are synthetically modified and synthetic materials. Natural or synthetic assemblies such as lipid bilayers, e.g., liposomes and non-phospholipid vesicles, are preferred. Among organic polymers of particular interest are polysaccharides, particularly cross-linked polysaccharides, such as agarose, which is available as SEPHAROSE™ (Pharmacia Biotech), dextran, available as SEPHADEX™ (Pharmacia Biotech) and SEPHACRYL™ (Pharmacia Biotech), cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Particles may also include diatoms, cells, viral particles, magnetosomes, cell nuclei and the like.

The particles will usually be polyfunctional or be capable of being polyfunctionalized or be capable of being bound to an sbp member through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a sbp member is employed, the manner of linking is well known and is amply illustrated in the literature. See for example Cautrecasas, *J. Biol. Chem.*, 245:3059 (1970). The length of a linking group may vary widely, depending upon the nature of the compound being linked, the nature of the particle, the effect of the distance between the compound being linked and the particle on the binding of sbp members and the analyte and the like.

As discussed above, the methods of the present invention include at least one step of actively moving one or both the first and/or the second SBP, by applying a force. A variety of techniques can be used to apply the force to move the first SBP member (e.g., the analyte) or the second SBP (e.g., the probe) in the methods of the present invention. For example, electrostatic, magnetic, gravitational, or hydrodynamic forces can be used. Techniques for applying such forces are known in the art and illustrates in the Examples herein. For example, the analyte can be electrophoretically moved to and from a membrane that includes a surface with bound probe molecules. As another example, the analyte is moved to and from the surface with a flow of liquid.

As an illustrative example, where a particle can be used to bind the analyte, centrifugal forces can be used to move the particle to and from the membrane that includes bound probe molecules. As another illustrative example, the particle can be a magnetic particle that can be moved to and from the surface in an uneven magnetic field. As another illustrative example, the particle is a charged particle that is moved to and from the surface by an electric field. To practically achieve delivery of analyte from a biological sample with a volume of ~1 mL within a time interval in the range from 10 sec to 15 min the velocities should be in the range of 0.1-0.001 cm/sec. Depending on size, charge and buoyant density of analyte or a particle used as a vehicle, the latter velocities can be practically achieved by applying forces 10 fN to 1 nN and more, as seen from Table 2 presented below.

As indicated above, methods of the invention in certain examples, include applying a second force or reversing the first force, to remove unbound or weakly bound analyte from the surface. Example 4, illustrates this aspect of the invention. Theoretical considerations regarding applying a force to remove unbound or weakly bound analyte to the surface are provided herein.

In another aspect, when the analyte is placed in fluidic connection with the probe molecule on a first surface, the analyte is immobilized on a second surface. For example, the surface with the immobilized probe molecule can be a stationary membrane, and the analyte can be immobilized on a particle. In an illustrative example, the particle with immobilized analyte is rolled or slid across the probe-covered surface of the membrane to allow the probe and analyte to bind, thereby capturing particles with bound analytes that are recognized by the probe. This rolling or sliding can be caused by the application of two forces, as discussed in further detail herein as the rolling stones method. The captured particles are then detected using one of the detection techniques discussed herein.

In certain aspects, methods of the present invention include allowing a self-forming density gradient to form in the reaction chamber (e.g., the channel). As described in more detail in Example 1, the presence of a density gradient reduces heat induced convection thereby improving performance of the methods of the invention. Example, 1 provides a variety of techniques that can be used to form a density gradient, including, for example, using a protein solution at an effective amount. An effective amount of protein for a self-forming density gradient is typically greater than 0.1 mg/ml, for example 1-10 mg/ml, such as 1 mg/ml, 5 mg/ml, or 10 mg/ml.

Methods for suppressing convection by forming density gradients represent another embodiment of the present invention. Accordingly, in one embodiment, the present invention provides a method for suppressing convection formed during an electrophoretic concentration procedure in free solution, by automatically forming a density gradient by including an effective amount of one or more proteins (e.g., 1 mg/ml BSA, dry milk or bovine Hb) to an electrophoresis solution. As illustrated in the attached Examples, upon electrophoresis at pH=8.5 with plus potential at the lower electrode these proteins migrate to the bottom of the cell forming a stable gradient of density. This gradient effectively prevents convection and allows antibodies to be collected in vicinity of the membrane at the bottom of the cell. Lowering the Hb concentration to 0.1 mg/ml or reversing the sign of the potential to make the protein concentrate at the top of the electrophoretic cell did not result in formation of stable density gradient and a convection was clearly visible.

Figure 7:
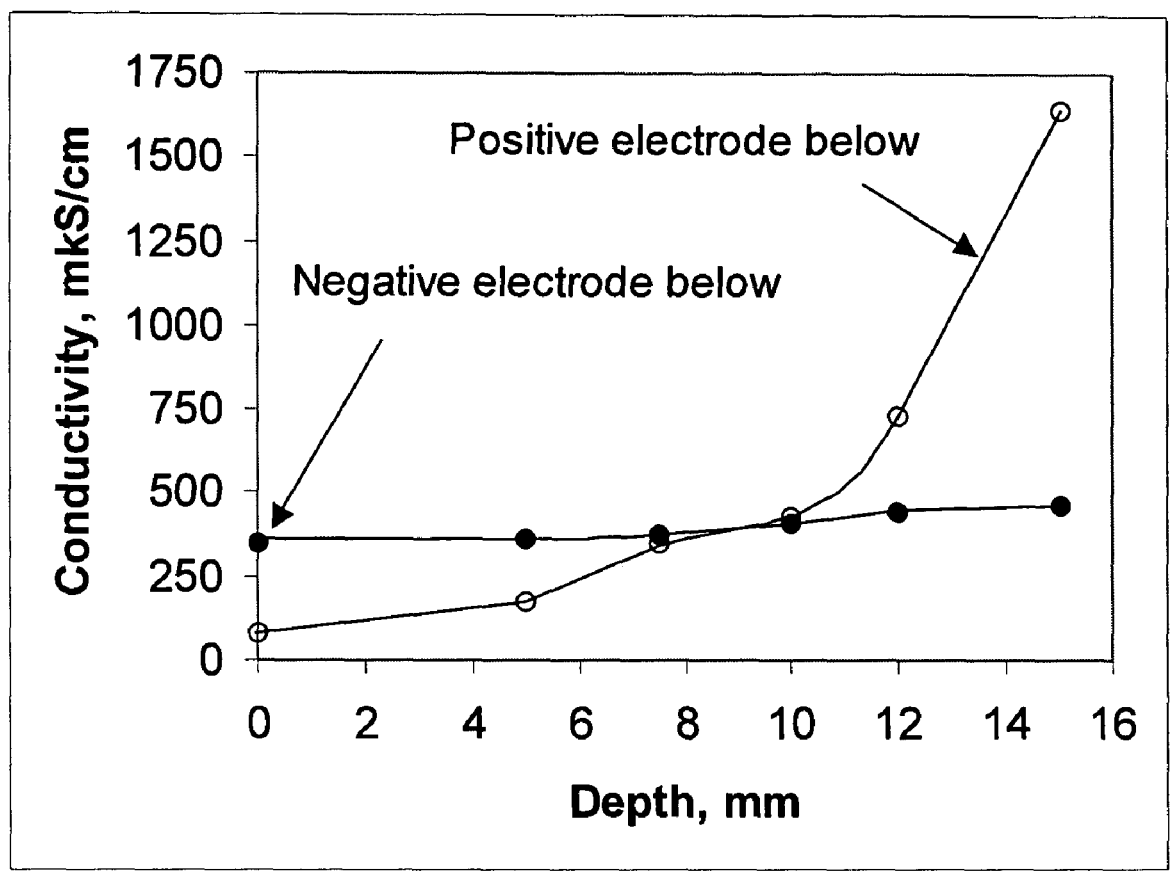
FIG. 7 illustrates the polarization of a dialysis membrane as factor stabilizing solution in the electrophoretic cell against convection. Distribution of solution conductivity in an electrophoretic cell after running electrophoresis in 5 mM Gly-Gly buffer, pH=8.5 for 10 min at 1.5 mA/cell with different directions of electric current. Conductivity was measured in 4 μL probes taken from different depths in 15 mm high electrophoretic cell. Voltage was changed from 120 to 190 V throughout the experiment to keep the current constant.

In another aspect of this embodiment, as illustrated in the Examples, a self-forming density gradient is established by applying an electrophoretic field to a buffer-containing solution across a dialysis membrane. The density gradient forms due to polarization of the dialysis membrane under certain conditions. As shown in FIG. 7, electrophoresis through a membrane with positive electrode in the lower electrode chamber results in accumulation of the buffer solution in the vicinity of the membrane, so that conductivity in the lower part of the electrophoretic cell is 10-20 times higher than in the upper part of the cell. Due to this conductivity strength of the electric field and generation of heat is smaller at the bottom of the cell as compared to the top. This results in formation of a temperature gradient inhibiting convection. Under typical experimental conditions the upper part of electrophoretic cells has a temperature that is 2-6° C. higher than that at the cell bottom, which is not different from room temperature. It was found that polarization originates from higher mobility of cations within the dialysis membrane as compared to that of anions, and the polarization-induced temperature gradient could be formed both in weak bases and weak acids as buffers. Virtually any buffer can be used in this aspect of the invention because by their nature, buffers include both cations and anions. For example, 5 mM Gly-Gly buffer (pH=8.5; negatively charged buffer ion), 10 mM ethanolamine (pH=8.5, positively charged buffer ion); 10 mM acetate (pH=5.5, negatively charged buffer ion) can be used. Similar polarization was observed with different types of buffer ions (e.g., with negative Gly-Gly at pH=8.5 and acetic ions at pH=5.5, and with positively charged ethanolamine ions at pH=8.5), in a non-buffered NaCl solution and in 10 mM NaOH. The polarization is reduced by about 50% after membrane treatment with a mixture of EDC and ethanolamine, which decreases the concentration of titrable acidic groups inside the membrane from 10 mM to 0.5 mM. No polarization was observed in 10 mM HCl solutions. No to be limited by theory, these last two observations strongly indicate that the polarization originates from cation-exchanging properties of the dialysis membrane.

In certain aspects of the invention, the analyte is bound to an artificial particle or forms a portion of a natural complex. As discussed above, a variety of particles, including artificial particles are known in the art. Examples of analytes incorporated into large natural complexes include, for example, receptors on cell surface, protein or polysaccharide antigens on virus capsids, antigens and allergens on pollen particles.

In certain aspects of the invention, as illustrated in the Examples herein, the probe is one of a population of probe molecules deposited on the surface as a microarray. The population of probe molecules, for example, can include different probe molecules deposited and immobilized in the microarray. Methods for depositing probes in a microarray are known in the art and illustrated in the Examples herein. In certain illustrative examples, the population of probe molecules is deposited as one or more bar codes or as one or more spots having a specific form to be visually recognizable and distinguishable. Instead of identification of a spot by its position (address), as is typical for microarray-based assays, spots can be visually identified by their form (bar code, letter), or size, provided each different probe is spotted in a different shape or size, thus making them easily distinguishable.

In certain aspects, the methods of the present invention include subjecting a particle, for example a particle that includes bound analyte, to the combined action of two forces in such a manner as to make it roll or slide (without rotation) over the surface to actively probe the surface for the presence of active sites. This aspect of the invention is illustrated and described in further detail in Example 11 and is referred to herein as the "rolling stones" technique. This technique can be used to facilitate detection of binding of analyte and probe by detecting particles such as beads, that bind to the analyte. The force applied to roll the particle depends on a number of factors, including the size of the particle, as discussed in Example 11. For a 1 μm particle, for example, a force of between 1 pN and 10 nN is typically employed, which moves the particles with a velocity ranging from 10 μm/sec to 1 mm/sec.

Figure 24:
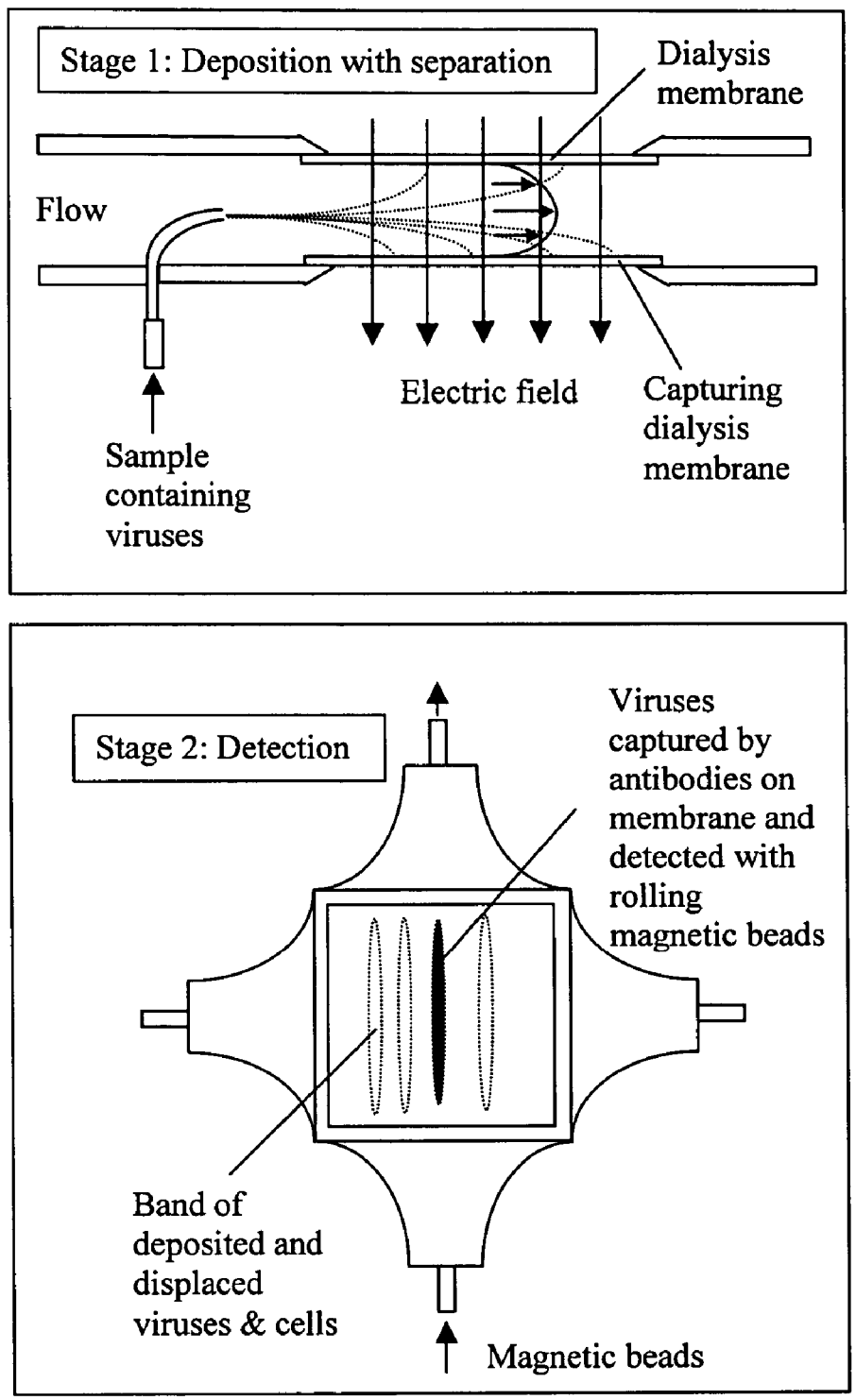
FIG. 24 provides a schematic of a device for active assay which performs two active stages: (1) capturing analytes with their separation (binding different analytes at different areas on membrane when analytes are moved by combination of flow and electric field), (2) detection of bound analytes with rolling beads bearing antibodies specific for the analyte.

Virtually any combination of forces disclosed herein can be used to roll or slide the particle over the surface. For example, flow and magnetic forces can be used to roll the particle over the surface. Therefore, for these embodiments, three forces are typically employed. FIG. 24, provides an illustrative example wherein an electrical force is used to move the analyte (e.g. virus) to the probe (anti-virus antibodies), and the bound viruses are detected by using magnetic and flow forces to roll magnetic beads that bind to the virus. The forces are typically oriented perpendicular to each other in order to creating the rolling motion, as will be understood. One example of this aspect of the invention, further includes recognizing and sorting a bead having the analyte captured on its surface by tethering the bead onto an array of antibody probes specific to analytes.

In a specific embodiment related to the "rolling stones" method, the present invention provides a method for detecting a biological molecule by rolling or sliding beads over a biochip. According to the method, a probe molecule is immobilized on a surface of a biochip, or immobilized on a membrane or in a layer supported by a substrate of a biochip. An analyte is then placed in fluidic connection with the probe molecule on the surface. The analyte is then subjected to the action of two forces one of which (normal) tends to move the analyte to the substrate surface and to facilitate contact and possibly binding of the analyte to the probe, while another force (tangential) pulls the analyte molecule parallel to the surface. These two force might be two components of one force (e.g., magnetic or centrifugal) directed at an angle to the surface so that both normal and tangential components are formed, or physically different forces can be employed to support motion of analyte in normal and lateral directions. Optionally, a second force can be applied or the first force can be reversed, to remove unbound or weakly bound analyte from the surface. Analyte that remains bound to the surface is then detected, for example using a particle with a bound specific binding pair member that, for example recognizes the analyte. The particle is passed over a track of the surface using two forces arranged to roll or slide the particle over the surface. The particle bound to the surface is then detected. The particle rolls over a surface when it not only moves across a surface, but also rotates about an axis as it moves across the surface. Though rolling is advantageous in making all the particle surface accessible to contact with probes, under some conditions (e.g., when particles are not spherical) combination of normal and lateral force components can be used to cause particles to slide over the substrate surface. Such a mode can also be used to effectively screen a substrate for probe molecules.

Various aspects of the present invention can be envisioned based on the examples and the general considerations provided herein. Specification illustrative examples of the present invention include the following:

ELISA in disposable cells with a dialysis film at the bottom in which primary and secondary antibodies are concentrated at the bottom with an electric field. It is shown that addition of certain blocking proteins and polymers as well as membrane polarization can be used to prevent convection inside the cell.

An active assay based on use of antigen (antibody) microarray deposited onto ultra-filtration or dialysis membrane at the bottom of a dialysis cell.

An active assay in which antigens or antibodies are detected on a substrate surface by probe molecules bound to particles. The particles are first pressed against the substrate by magnetic or centrifugal forces and then actively pulled off the surface by reversing the force.

An active assay in which analyte application and its removal are combined in one operation by shifting the point of action of a local force which pulls a stack of magnetic beads over the substrate surface (similar to the Xerox process)

An active assay in which analyte molecules bound to the surface are probed by particles covered with analyte-specific molecules using a procedure which includes rolling or sliding particles over the surface under action of two differently directed forces to rapidly scan the surface for the presence of the bound analyte molecules, cells, cell fragments or viruses.

An active assay in which many different probes (antigens and antibodies) are arrayed onto a substrate and the microarray is used in active multi-component assay.

An active assay in which different active processes are combined in one procedure. In one such procedure analytes (molecules, viruses or cells) are first actively concentrated in a compartment where they bind magnetic beads. The beads are further actively pressed or rolled over a substrate covered with linked probe molecules capable of tethering beads containing bound analytes.

As indicated above, methods of the present invention, in certain aspects, detect binding of an analyte to a probe. An "analyte" is a compound or composition to be detected. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus. In certain aspects of the invention, the analyte is charged.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

A member of a specific binding pair ("sbp member") is one of two different molecules, having an area on the surface or in a cavity which specifically binds to and is thereby defined as complementary with a particular spatial and polar organization of the other molecule. The members of the specific binding pair are referred to as ligand and receptor (antiligand) or analyte and probe. Therefore, a probe is a molecule that specifically binds an analyte. These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Specific binding is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

Non-specific binding is non-covalent binding between molecules that is relatively independent of specific surface structures. Non-specific binding may result from several factors including hydrophobic interactions between molecules. The methods of the present invention, as indicated above, typically include a step wherein a first SBP member that is non-specifically bound to a second SBP member is actively separated from the second SBP by the application of a force.

Many detection methods are known in the art and can be used in the methods of the present invention for detecting an analyte bound to a probe on a surface. In some aspects, the antibody and probe complex is removed from the surface before being detecting, although typically the probe and antibody complex is detected while it is bound to the surface. The detection can be, for example, visual, spectrophotometric, or microscopic. Illustrative detective methods are provided herein. In certain examples, detection uses an enzymatic reaction, as is well-known in the art.

In certain detection methods, light from a light source is passed through the activated membrane and a change in light, such as absorbance at a certain wavelength, or fluorescence, is detected by a detector. In certain illustrative embodiments for these aspects of the invention, the activated membrane is transparent. In other examples, luminescence is detected.

Figure 23:
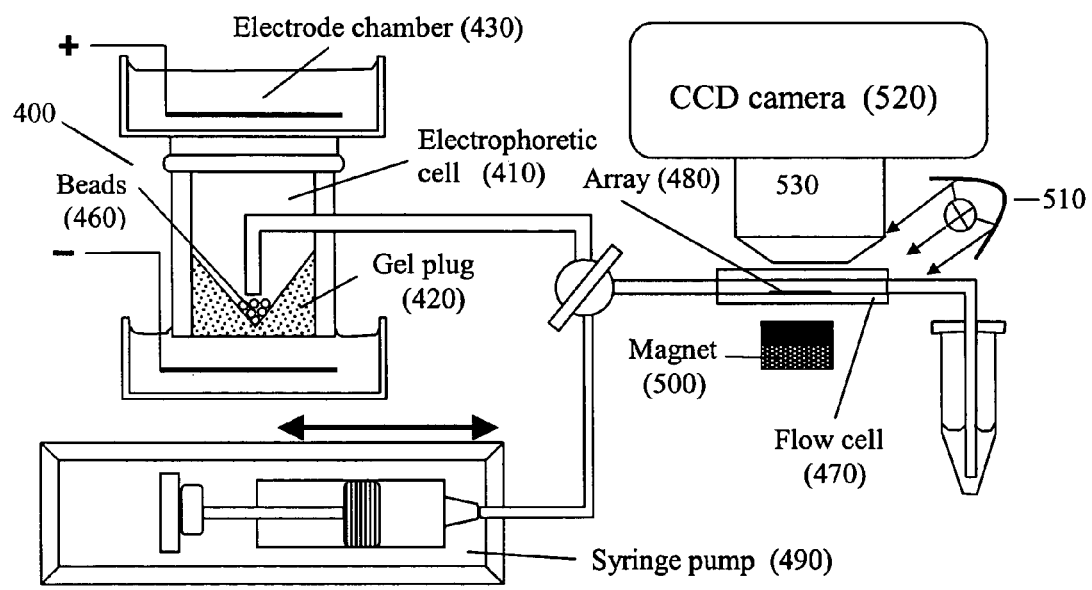
FIG. 23 provides a schematic of apparatus for active assay in which analyte is first concentrated onto capturing beads and then actively recognized and detected by a "rolling stones," also referred to as a "rolling beads," technique on a microarray.

In certain aspects of the present invention, where a particle is rolled or slid over an activated surface that includes a probe, the detection method can detect the particle, as illustrated in FIG. 23. Methods are well-known in the art for detecting particles by detecting, for example, light scattering, fluorescence, or magnetic resistance to an electrical current. For example, to detect light scattering, a microscope can be used, for example a dark field microscope. In certain examples, fluorescent particles can be used and detected using UV illumination. In another example, magnetic beads can be detected electronically using sensors, such as BARC sensors, that detect changes in magnetic resistance.

In certain aspects of the apparatuses of the present invention discussed below, the apparatus includes a detection system, as illustrated, for example, in FIG. 23. The detection system can be, for example, a light source and a light detector positioned such that light emanating from the light source passes through the activated membrane or reflects off the activated membrane and is detected by the light detector. The light detector, for example can measure light absorption or can be a microscope and a digital processor used to capture the image of a surface of coated beads for computer analysis.

Three main features distinguish a method of the present invention, (i.e., an active bioassay) from a standard bioassay:

Moving analyte to and from probe molecules. In the standard assay analyte molecules diffuse in a concentration gradient;

Concentrating analyte in a probe compartment. No concentration is achieved in standard passive methods; and Detaching weakly bound analyte molecules and actively transporting them out of the probe compartment. Detachment of weakly bound analyte molecules in the standard methods is a result of thermal fluctuations. Detached molecules are further washed away by diffusion or re-associate with probe molecules.

Not to be limited by theory, the following paragraphs provide theoretical considerations that are relevant to these distinguishing features of the methods of the present invention. Different realizations of an active bioassay are presented as well as estimates of the forces necessary for active processes. As indicated above, the methods of the present invention typically are performed by applying a force to the analyte to move it to and from a probe.

Forced transport vs. diffusion in a concentration gradient. A radical way of solving both diffusion problem and affinity limitations in assay systems is to replace diffusion with an active transport process.

Applying a force F to each analyte molecule makes them move with an average velocity:

$$V=uF \qquad (5)$$

Where $u=D/kT$ is mobility, k is the Boltzmann's constant and T is absolute temperature.

Forced flow of analyte to the surface is expressed by the Eqn:

$$J_v = C_o V = C_o FD/kT \qquad (6)$$

The flow due to passive diffusion in the concentration gradient:

$$J_d \sim DC_o/\delta \qquad (7)$$

Thus, forced flow of analyte to the surface exceeds that of passive flow by a factor:

$$M = J_v/J_d \sim F\delta/kT \qquad (8)$$

As one can see, this acceleration depends neither on analyte concentration nor on diffusion coefficient of the analyte. It is a ratio of the work of the force on a distance of the unstirred layer to kT.

In the above presented example $\delta=25$ μm and application of electric field with $E=10^4$ V/m, to a protein molecule with $Z=5$ charges will accelerate analyte/probe reaction by a factor of $M=EZe\delta/kT=53$ fold.

Different forces can be used to move analyte molecules, particles covered with the analyte molecules or particles including the analyte molecules as integral part (e.g., bacteria or virus antigens). We will consider some of them below.

Electroconcentration of Analytes in Vicinity of an Semi-Permeable Surface.

Active transport can be also used to accumulate reagents in certain compartments of a device and increase the local concentration there. This will allow to overcome the affinity limit in the immuno-assay.

If an impermeable membrane is placed on the way of the analyte molecules moving in an electric field, E, the latter are accumulated at the boundary creating a gradient of concentration which generates a passive diffusion directed against the active flow. When these two flows counterbalance a stationary gradient of concentration is established. The stationary concentration profile can be obtained by solving the flow-diffusion equation (Fick's second law of diffusion):

$$\partial C/\partial t = D(\partial^2 C/\partial^2 x) - (EeZ/6\pi\eta R)\partial C/\partial x = 0 \qquad (9)$$

Here E is the electric field strength, eZ is the charge of analyte molecules, $6\pi\eta R$ is the frictional coefficient of a particle with radius R, which is moving in a medium of viscosity $\eta$. In the simplest case of one-dimensional electrophoretic process the solution is easily obtained (Chen et al., 1976):

$$C(x) = \beta L C_o \exp(-\beta x) \qquad (10)$$

$$\beta = EeZ/6\pi\eta RD = EeZ/kT \qquad (11)$$

Consider a practical example of electrophoretic concentration of protein molecules at a semi-permeable membrane closing the end of a capillary filled with a protein solution. Protein molecules with Z=5 charges moving in an electric field of $E=10^4$ V/m in a L=1 cm long capillary will reach stationary concentration profile $C(x)=2\times10^4$ CO exp ($-2\times10^6 x$) and in vicinity of the membrane (x=0) protein concentration will be increased 20,000 times. Potentially this will increase the sensitivity of assay far beyond the natural affinity of the probe molecules. This concentrating effect will be reached in approximately $\tau \sim 3\pi\eta\alpha L/eZE = 5$ min.

Magnetic Forces.

Magnetic field can be used to move analyte molecules bound to paramagnetic or ferromagnetic beads by applying an uneven magnetic field. Magnetic force can be estimated as:

$$F = M(B)v\,\mathrm{grad}B \qquad (12)$$

Where B is magnetic field, M(B) is the bead magnetization, v is the bead volume. Magnetic field generated by the modern rare earth permanent magnets reaches 10,000 Gauss. Magnetite ($Fe_3O_4$) beads, 0.8 μm in diameter are subjected to a force of 0.4 pN in the field of such a magnet (Lee et al., 2000).

Centrifugal (Gravitational) Forces.

Bulky analyte molecules, beads, cellular fragments, viruses and whole cells can be moved by centrifugal force. Modern centrifuges allow to reach acceleration up to G=600,000 g. Applied to cellular fragments containing analyte molecules (e.g., surface antigens of bacteria or viruses) or artificial beads covered with immobilized analyte molecules centrifugal forces generate a force proportional to the buoyant density of the particle, $(\rho-\rho_o)$, and its volume, v:

$$F_g = v(\rho-\rho_o)g \qquad (13)$$

The velocity depends on viscosity of the liquid ($\eta=10^{-3}$ kg/sec m for water) according to the Eqn:

$$V_t = F_g/6\pi\eta R \qquad (14)$$

For example, for a polystyrene particle with a radius of R=0.5 μm and a density $\rho=1.05$ g/cm³ $F_g$ will reach 2.6 pN at 10,000 g, and such particles will be collected in 1 cm long cell in 36 sec, whereas magnetite particles ($\rho=5$ g/cm³) of similar size at the same acceleration, g, will be subjected to a force of 205 pN and will sediment in 1 cm long cells during 0.4 sec.

A cell with R=5 μm and $\rho=1.07$ g/cm³ is subjected to force of ~360 pN at acceleration corresponding to 1,000 g and its sedimentation in the tube 1 cm long will take only 0.4 sec. Thus, centrifugal forces enable rapid collection of dense particles and cells and generate forces large enough to discriminate between specific and non-specific interactions.

Other forces, like dielectrophoresis, can also be used to actively transport analyte molecules to probe molecules to overcome diffusion limit in assay.

Hydrodynamic Forces.

In contrast to electrostatic, magnetic and centrifugal forces the hydrodynamic force have limited application since these cannot be as easily operated (reversed, for example) as the former ones. Nevertheless, they can be used in some particular assay described below and here we present a short fundamentals of the hydrodynamic forces.

A spherical particle of radius R in contact with a plane wall in a laminar linear flow is subjected to a drug force (O'Neil, 1968):

$$F_d = 10.2\pi\eta RU \qquad (15)$$

$U(R) = V_{max}[4R/h - (2R/h)^2]$ is the fluid velocity at a distance R from the wall (Luthi et al., 1998). Here h is the distance between walls in a flow cell, $V_{max} \sim (3/2)V_m/bh$ is the maximum velocity in the middle of the chamber with width b, and $V_m$ is a mean velocity, which is the ratio of the volume velocity to the chamber cross-section, bh. In a numerical example of a water flow with a volume rate of 0.1 mL/sec through a flow chamber with a cross-section of 4×0.03 mm a spherical particle with a radius of R=0.5 μm adherent to wall is subjected to a drag force of 1.3 nN. Considering further that the particle is bound to the surface with a link, l=10 nm long (see FIG. 1), one can estimate that the drag force should be counterbalanced with a force applied to such link which is by a factor of $(R/l)^{1/2}$ higher than $F_d$. With l=10 nm and R=0.5 μm force applied to link will exceed the drag force by a factor of 7. These simple estimates show that hydrodynamic forces can be used to break even multiple specific bonds as well as to selectively remove weakly bound particles from the substrate surface.

Concentration factor in the reaction between analyte molecules immobilized on a bead and probe molecules immobilized on a substrate. Concentration factor can be estimated as following. Let us assume that beads are covered with analyte molecules linked to the bead surface via a polymer spacer with length l. Let us also assume that the substrate is also covered with probe molecules immobilized in a similar way. Upon a contact of such a bead with the substrate a contact area is formed with a radius, $b=(2\,l\,R)^{1/2}$ in which immobilized probe molecules and analyte molecules can reach each other. Assuming that all the interactions proceed in an layer of thickness, l, one can estimate the local concentration of analyte and probe molecules in the contact area as a $C_s/l$, where $C_s$ is the surface density of bound molecules. Taking into account that one protein molecule available for antibody binding occupies approximately 100 nm² of surface in a typical solid-phase immunoassay (Balcells et al., 1999) one can easily estimate that in the contact area of a bead with radius of 0.5 μm, and l=10 nm local concentration of probe and analyte molecules will reach ~1 mM. Were no considerable steric problems imposed for the reaction between approximately 100 probe and analyte molecules in the contact area the interactions should be established within $\tau=[k_{ass}(C_s/l)]^{-1}=[10^9 \times 10^{-3}]^{-1}=10^{-6}$ sec.

Experimental estimates for the association constants in a contact between HSA-coated surface and the AFM tip bearing anti-HSA antibodies yielded $k_{ass}=5\times10^4$ $M^{-1}$ $s^{-1}$ (Hinterdorfer et al., 1996), which is $2\times10^4$ times smaller than value taken in the estimate presented above. Similar estimates for $k_{ass}=10^3-10^5$ $M^{-1}$ $s^{-1}$ were found for interaction of VE-cadherin strands immobilized on AFM tip and on mica (Baumgartner et al., 2000). Nevertheless, even with this reduced association constant interaction between the bead and surface will proceed in the previous example within 20 msec.

Binding of Particles to a Surface. Origin of Background.

Rough estimates presented in the previous paragraph well illustrate origin of nonspecific binding in a bead assay. Considering large local concentration of interacting molecules even relatively weak interactions will come into play upon direct contact of bead with surface and beads may bind surface via many weak non-specific interactions. Even polymers considered as inert with respect to protein binding still have some affinity to proteins. For example, an attractive interaction has been recently demonstrated between a layer of poly (ethylene glycol) and streptavidin (Sheth, & Leckband, (1997)), which was previously claimed to be negligible (Sofia et al., 1998; Pieler et al., 2000). Without differentiation between such non-specifically bound beads and the ones which bind the substrate via strong specific interactions it is difficult to reach good sensitivity, since the sensitivity limit is determined with the smallest number of specific interactions recognizable. Such discrimination can be made by applying a force which is strong enough to break non-specific interactions but incapable of breaking specific interactions and, thus, leaving on the substrate only those beads which are bound via specific interactions. This raises a question about a scale of forces responsible for specific and non-specific interactions.

Breaking Bonds. Recognition of Specific Interactions.

Active bioassay is essentially relied on discrimination between specific and non-specific bonds. Physics of ligand-receptor interactions was thoroughly reviewed in Bongrand (1999) and Mammen et al. (1998). Table 1 presents a scale of forces needed to break different biospecific interactions. These, of course, should be considered as rough estimates since many factors shortly outlined below are capable of affecting the force value.

TABLE 1

Unbinding forces for different biospecific interactions.

| Bond | Method of measurement | Force, pN | Note | Reference |
|---|---|---|---|---|
| Streptavidin-biotin | Forces between bent mica sheets and AFM | 90-250 | Effect of linker is studied. | Wong et al., (1999) Wong et al., (1997) |
| BSA - antiBSA | AFM | 240 | Lifetime of loaded bond and association constants are determined | Hinterdorfer et al., (1996) |
| Florescein-Antibody | AFM | 40-160 | Depends on the loading rate | Schwesinger et al., (2000) |
| Ig G— protein G | Measurement of cell adhesion | 11 | | Kwong et al., (1996) |
| F-actin | Flexible glass rod | 108 | | Kishino & Yanagida (1988) |
| To unzip ds-DNA | Microneedle bending | 13-17 pN | | 2. Essevaz-Roulet et al., (1997) |

Non-specific interactions include van der Waals interactions, hydrophobic, electrostatic interactions. Their theoretical estimates are difficult and we limit ourselves to few known examples in which nonspecific interactions were estimated. Thus, non specific interactions of beads with polystyrene surface covered with immobilized antibody-streptavidin conjugate via PEG linkers and a polystyrene surface covered with another antibody-streptavidin conjugate were easily broken by applying force of about 0.4 pN (Lee et al., 2000). Since they have nearly identical surfaces and interaction was performed in 50 mM phosphate buffer with 0.15 M NaCl electrostatic interactions were negligible in this case. Direct van der Waals interaction was also considerably reduced since the direct contact of polystyrene sphere with the polystyrene surface was mediated via a layer of linkers and protein molecules. This example clearly demonstrates that careful choice of conditions enables a suppression of non-specific interactions to sub-pN level.

Irreversible Breakage.

Bond breakage is a complex thermally activated process. It has been shown that probability of bond breaking as well as destruction of many materials subjected to stress can be described with an universal function (here presented as a dissociation constant):

$$k_d(F) = k_{do} \exp(\sigma_d F/kT) \quad (16)$$

Here $\sigma_d$ has a meaning of an effective length at which the external force works to help to overcome the reaction barrier. Its value varies between 0.4 nm and 0.1 m for fluorescein-antibody complex according to Schwesinger et. al., (2000). With the force increasing linearly with time, F=rt, the most probable unbinding force is (Schwesinger et. al., 2000):

$$F_m = (kT/\sigma_d) \text{Ln}(r\sigma_d/k_{do}kT) \quad (17)$$

Average time needed to break half of the bonds loaded with a constant force, F, is:

$$T(½) = (\text{Ln } 2/k_{do}) \exp(-\sigma_d F/kT) \quad (18)$$

Force values presented in Table 1 reflect conditions where time of the bond breakage was reduced from its initial value of $T \sim 1/k_{do}$ (~6 min for $K_d = 10^{-9}$ M, (Schwesinger et. al., 2000))) to $T \sim (1/k_{do}) \exp(-\sigma_d F/kT) \sim 1$ sec or less. It should be kept in mind, that the unbinding force will decrease if the bond is subjected to an external force for a longer time as it follows from the Eqn. 18.

Reversible Breakage.

Previous estimates were based on assumption that ones broken the bond does not re-associate, which is true only for large forces. Effect of small load incapable of affecting dissociation reaction may, nevertheless, be notable since small forces can effectively prevent re-association. Accounting for the effects of external forces on binding equilibrium is important in understanding processes of active washing, when unbound analytes are pulled away from the surface by external force. This account cannot be done as simple as for breaking of loaded bond described above. External force applied to move analyte from the surface will decrease the probability of its returning to the surface the more the longer is the distance, x, between the molecules and the surface.

$$P_x = P_o \exp(-xF/kT) \quad (19)$$

Thus, primary effect of the external force is directed on destruction of the "cell effect" (Medvedev, 1992) which describes the situation when once broken bond is soon restored due to slow diffusion of the molecules apart.

Case of Multiple Bonds.

When analyte molecule or a bead is attached to a surface through a number of parallel bonds the situation is more complex, especially if the bonds are formed via different spacers and thus different complexes are subjected to stress at different distances between bead and surface as illustrated in FIG. 1.

Formation of multiple bonds results in increase of the effective unbinding force. Thus, Ludwig et al., 1997)

observed that average adhesion force between the biotinylated tip and streptavidin coated substrate was equivalent to ~1,000 pN, which exceeds 4 times the rupture limit of the individual molecular pairs. Case of multiple bonds has been analyzed both theoretically and experimentally in many studies, since measurements of cell adhesion are mostly dealing with multiple interactions (Piper et al., 1998; Baltz & Cone 1990; Chen et al., 1997; Mammen et al., 1998).

To some extent the situation with multiple bonds is similar to the "cell effect" mentioned in the previous section. Once broken the bond has a good chance to recover since the beads is held close to the surface by other bonds. It is, thus, expected that in the case of multiple bonds formed between biospecific molecules on long spacers much larger forces will be required to disentangle contact between beads and surface Scale of forces which can be applied using different techniques is summarized in Table 2. One can see that electrostatic forces acting on a typical protein molecule are too weak to directly affect specific protein-protein interaction (see Table 1). Micron-sized charged particles placed in a strong electrostatic field cannot break a single antigen-antibody bond, as well. Magnetic forces are strongly dependent on the size of beads. Small beads can only break weak interactions. With a bead diameter of 3-5 μm magnetic forces are high enough to break single antigen-antibody bond. It is interesting to note, that centrifugal forces can break such bond when bead is 1 μm in diameter, provided the bead is made of a dense material. Beads with such size can be subjected to the largest forces in a shear flow: even multiple specific bonds can be broken. Thus, not only discrimination, but complete erasing of the detection signal becomes possible.

TABLE 2

Comparison of forces providing with different techniques.

| Type of force | Example of analyte or vehicle | Force, pN |
|---|---|---|
| Electrostatic[a] | Protein molecule, Z = 5 in a field E = $10^4$ V/m. | 0.008 |
| Electrostatic[b] | Carboxylated polystyrene bead, 1 μm in diam. and zeta potential, ξ = 30 mV, in a field, E = $10^4$ V/m. | 0.16 |
| Magnetic[c] | $Fe_3O_4$ bead 1 μm in diam. in a field of a rare earth magnet. | 0.4-7 |
| Gravitational[d] | $Fe_3O_4$ bead, 1 μm in diam. at 10,000 g. | 205 |
| Gravitational[d] | Polystyrene bead, 1 μm in diam. at 10,000 g. | 2.6 |
| Hydrodynamic[e] | Spherical bead, 1 μm in diam. in a flow cell, 100 μm thick, with maximum velocity 0.3 m/sec. | 100-700[f] |

Footnotes to Table 2
[a]Force is calculated as F = EeZ; e is elementary charge, Z is the average number of charges per molecule.
[b]The value of F is estimated using the Helmholz-Smoluchovsky equation for the zeta potential: $\xi = (4\pi v\eta/\epsilon\epsilon_o E)$ and the expression, $v = F/6\pi\eta R$ for the velocity of a particle with radius, R. Here η = 1 mPas is the viscosity of water, $\epsilon$ and $\epsilon_o$ are the dielectric constants of water and absolute dielectric constant, respectively.
[c]The value of 0.4 pN is for 0.85 μm beads according to Lee et al., (2000), 7 pN is obtained in our own measurements of force with which a rare earth magnet attracts 4 mg of dry beads, 1 μm in diameter, prepared from $Fe_3O_4$.
[d]This value is calculated using Eqn. 13 by taking $\rho_o = 1$ g/cm³ for density of water, $\rho = 1.05$ g/cm³ and $\rho = 5$ g/cm³ for density of polystyrene and magnetite, respectively.
[e]Shear flow force is calculated according to Eqn. 15.
[f]The last figure is calculated by assuming that the force applied to the bond is $\sim(R/l)^{1/2}$ times greater than the force applied to the bead. The length of the linker, l, is taken as 10 nm.

Figure 8:
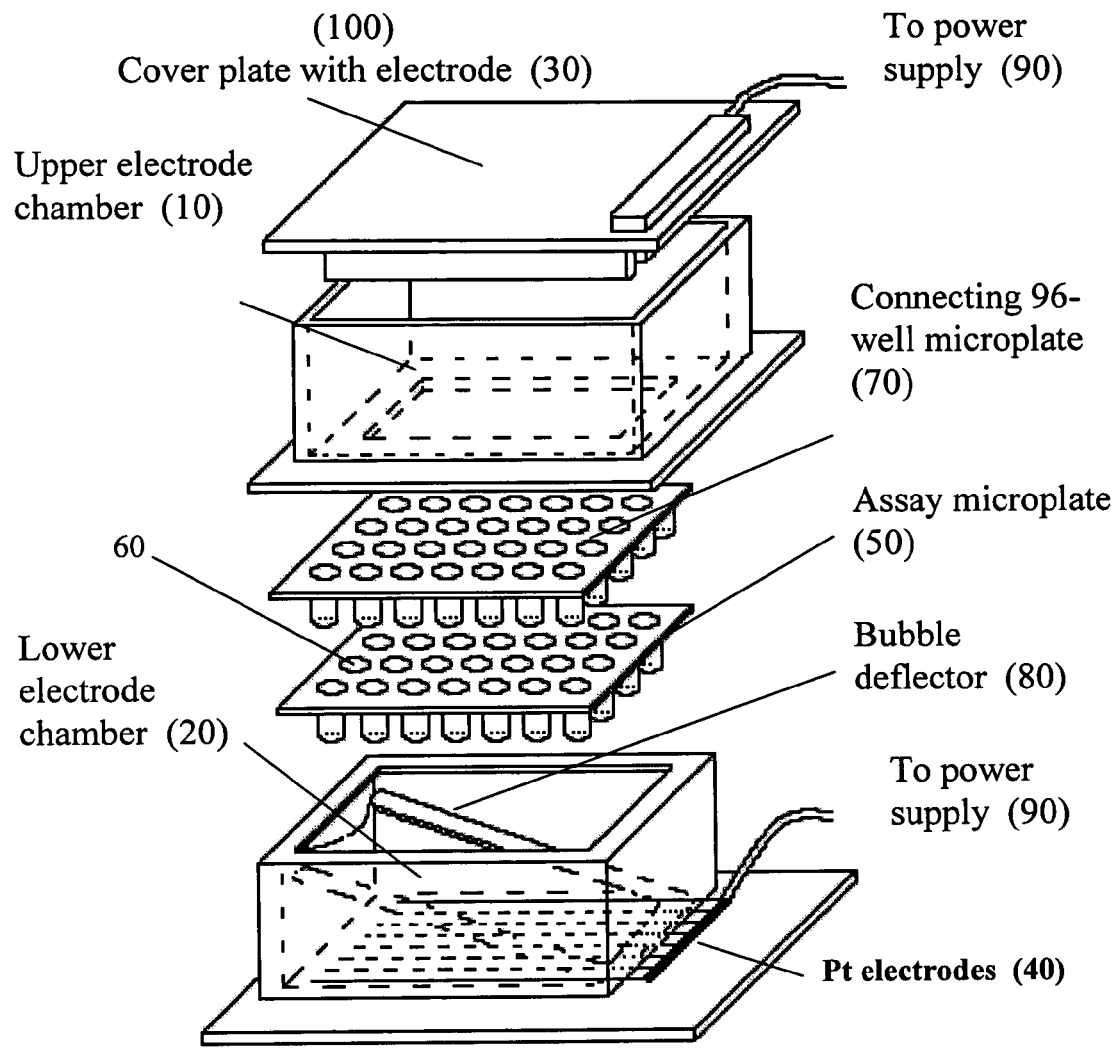
FIG. 8 provides a Schematic of an apparatus for electrophoretically enhanced immunoassay in 96-well microplate.

In addition to embodiments directed to methods for performing active assays, the present invention provides an apparatus or device for performing an active assay method of the present invention, such as active electrophoresis. An example of an apparatus of this embodiment of the invention is shown in FIG. 8. The apparatus includes the following:
an upper (10) and a lower electrode chamber (20);
an electrode system (30 (upper) and 40 (lower)) disposed in the upper (10) and lower (20) electrode chamber;
a plurality of channels (60), for example formed from wells of a multi-well microplate (50), through which passes an electrical current provided by the electrode system (30, 40);
a plurality of activated, semi-permeable surfaces positioned across the plurality of channels such that the electrical current passes through the semi-permeable surfaces; and optionally
a deflector (80) disposed in the lower electrode chamber (20), wherein the deflector (80) is effective for deflecting away from the bottom of the channels, gaseous electrochemical products that form in the lower electrode chamber (20).

The activated, semi-permeable surfaces can be formed by a semi-permeable bottom of each well of a multi-well plate, such as, but not limited to, a 96-well plate.

In certain aspects, the apparatus includes a multi-socket connector (70) matching the wells of the microplate (50). The purpose of the connector (70) is to supply current individually to each well while preventing contamination of wells by the content of neighboring wells. The connector is physically attached to the upper electrode chamber so that current from the upper electrode is evenly distributed among the sockets. The channels can be formed in many different ways: (i) an array of holes can be drilled in a plastic; (ii) an array of droplets can be deposited onto a semi-permeable membrane; (iii) droplets of analyte solution can be applied to the external surface of sockets in the plate (70), while assay plate (50) is replaced by a semi-permeable membrane on which probe molecules are arrayed in such a way as to match array of sockets. In the latter case channels are formed upon contact of analyte droplets hanging from the sockets with the array of probes on the membrane.

The electrode system is connected to a power supply (90).

As indicated above, an apparatus of the present invention can include a deflector to protect the semi-permeable bottom from accumulation of bubbles. The deflector typically includes a frame with a porous membrane, such as a dialysis membrane (bubble deflector). The deflector is typically inserted into the lower chamber at an angle of about 30-50° relative to the microwell plate, for example as shown in FIG. 8, to deflect bubbles to the chamber wall.

In certain illustrative examples of the present invention, a dialysis membrane is attached to the bottom of the wells in the microplate and to the bottom of the wells of the connector to form the semi-permeable bottom of the multi-well microplate (50) and the liquid tight sockets of the connector (70).

In certain aspects, the apparatus further includes a layer of a gel positioned into wells (sockets) of the connector (70) to make it water tight but electrically conductive. At least a portion of the channels on the assay plate (70) can be submerged into a lower electrolyte solution and the solution can be stirred to increase heat exchange.

In certain aspects, a guide system is introduced to properly position the microplate and the multi-socket connector. The guide system includes a system of mounting posts on the top of a lower electrode chamber matching a system of fingers at the bottom of the upper electrode chamber. Insertion of fingers into posts enables exact positioning of the two chambers as well as exact positioning of an array of sockets in the plate (70) over an array of wells in assay plate (50).

In a specific aspect, the present invention provides an apparatus for performing an active assay, that includes the following:
a first cell with a semi-permeable layer connected to two electrode chambers;
a means to connect the first cell to a microfluidic system;

a microarray of probes integrated into the microfluidic system;

a means to actively move functionalized beads to and from the microarray or roll them over the microarray surface; and an imaging means for detecting beads bound to the microarray.

Figure 21:
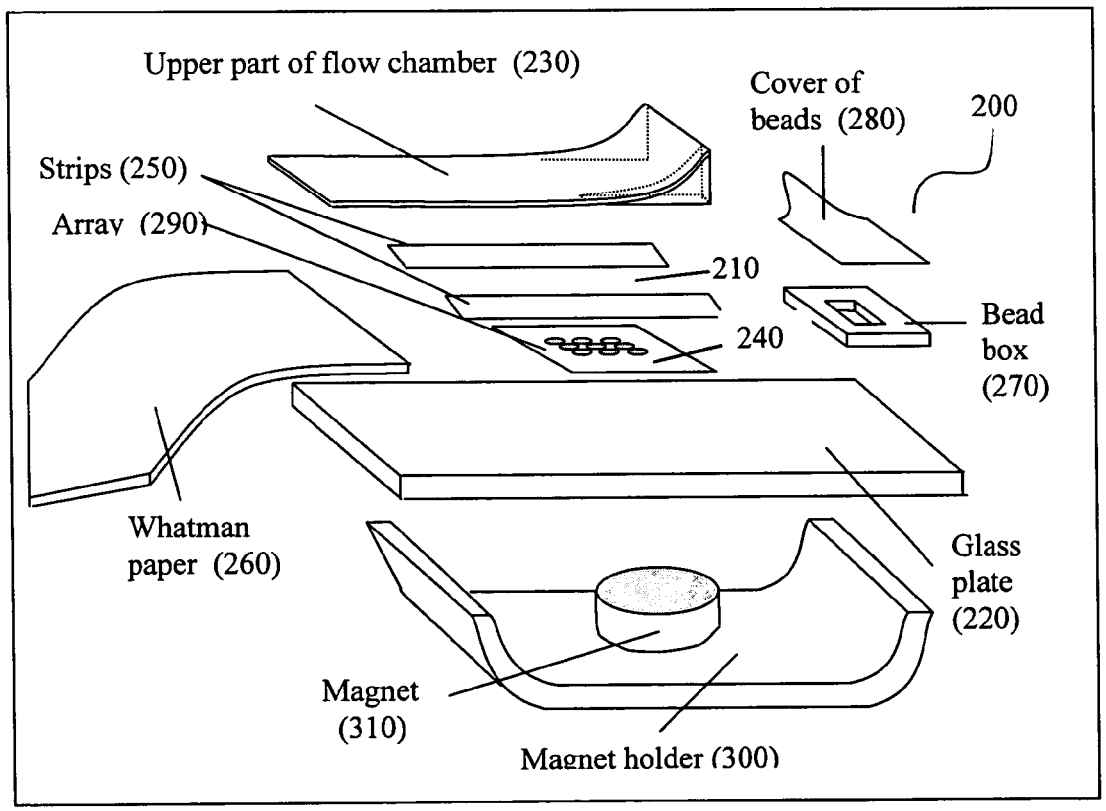
FIG. 21 provides an exploded view of a disposable flow-through chip for rapid diagnostics which employs "rolling beads" technique to detect primary antibodies captured on an antigen (antibody) microarray.

The Examples provided herein, including FIGS. 21 and 23, illustrate various means for connecting the first cell to a microfluidic system, illustrate a means for integrating a microarray of probes into a microfluidic system, and illustrate various means to actively move functionalized beads to and from the microarray by rolling the beads. This apparatus can be used, for example, to carry out the "rolling stones" embodiment of the present invention.

The semi-permeable bottom can be formed from a porous membrane, such as, for example, a dialysis membranes from regenerated cellulose, as disclosed herein. The membrane can be treated in plasma discharge for an effective time, for example 50 seconds, so that the membrane can actively bind biological molecules, as described in more detail herein.

The electrodes can be, for example a system of parallel platinum wires to evenly distribute current among all the wells. These wires can be attached to a cover (100) of the first chamber, or upper chamber (10) and to the bottom of the second chamber, or lower chamber (20).

One advantage of using a multi-well microplate to form the channels is that this feature makes the apparatus compatible with other standard apparatuses used in ELISA. Thus, for example, optical density in the wells with membrane bottom can be readily measured using a standard automatic microplate reader.

In another embodiment, the present invention provides an assembly for performing an electrophoretically-assisted assay. The assembly includes the following:

an upper and a lower electrode chamber;

an electrode system disposed in the upper and lower electrode chamber, a plurality of channels through which an electrical current generated by the electrode system passes; and a plurality of semi-permeable membranes each having an activated surface, wherein the semi-permeable membranes are positioned across the channels such that current passing through the plurality of channels, passes through the plurality of semi-permeable membranes, and wherein the semi-permeable membranes are penetrable for salt and buffer ions, but not for protein or polynucleotide analytes.

In certain aspects, the assembly includes a deflector disposed in the lower electrode chamber, wherein the deflector is effective for deflecting away from the bottom of the channels, gaseous electrochemical products that form in the lower electrode chamber. In certain aspects, an array of probe molecules is bound to each semi-permeable surface.

In another embodiment, the present invention provides a plate for an active assay. The plate includes a plurality of channels and a plurality of semi-permeable surfaces with activated surfaces positioned across the channels, wherein each membrane of the plurality of semi-permeable membranes is positioned across a channel of the plurality of channels.

In certain aspects, a probe or a plurality of probes, is bound to the surface of the semi-permeable membrane. The plurality of probes, for example can be an array of probes that are bound to each surface of the plurality of semi-permeable membranes. In certain examples, the analyte is a protein or a nucleic acid.

In another embodiment, the present invention provides a biochip and biochip assembly as illustrated and further disclosed in FIG. 21 and Example 12. The biochip and biochip assembly is designed for performing an active method of the present invention, particularly a "Rolling Stones" method. With reference to FIG. 21, the biochip assembly (200) includes a chamber (210) that includes a first surface (240) forming the bottom of the chamber, and a second surface (230), forming the top of the chamber. The first (240) and second surfaces (230) are separated by a gap. The gap is small enough and the surfaces hydrophilic enough so that the gap can be filled with a sample by capillary forces. The first surface (240) is formed from an upper surface of a substrate such as a glass plate, or polymer film including a semi-permeable membrane. The second surface (230) is formed by the lower surface of a plate held above the substrate by strips (250), which form the side walls of the channel. A microarray (290) of probe molecules is present on the first surface (240). If probes are arrayed on a flexible substrate (like a typical semi-permeable membranes) the latter can be kept flat by its gluing to a plate (220) preferably made of a rigid transparent material (e.g., glass or plastic). The chips can be assembled on a plate 1"×2-3" for convenience of handling. The number of probe spots on the microarray, 0.5"×0.5", can be as large as 100,000, although few spots, such as 12 or 24 spots, for example, can be used. Depending on analyte concentration 50-1,000 µL of reagents are typically required to perform an assay on such biochip assembly.

A piece of filter paper (260) placed near a first end of the gap is used to adsorb solution after it passes through the chamber. Positioned near the other end of the gap, is a small closed compartment (270), also referred to as a bead box, with a cover (280). The bead box contains a suspension of functionalized beads, such as dry magnetic beads. The compartment in certain examples is made of plastic. A magnet holder (300) holds a magnet (310) under the protein array.

A common microscope equipped with a dark-field condenser can be used for imaging individual tethered beads. A simple microscope with a dark-field illumination and a magnifier can be used as an inexpensive means to allow semi-quantitative reading of the disposable chip of this embodiment of the invention.

The following paragraphs present additional aspects of the active assays and apparatuses of the present invention.

Use of Beads as a Renewable Substrate to Actively Capture Analytes from Solution. Apparatus for Active Electrophoretically-Assisted Capturing Analytes on Beads.

Instead of being concentrated on a semi-permeable membrane with probes bound to the surface of the latter and then detected with beads, one can first concentrate and bind analyte on beads and then actively detect and recognize beads with the bound analytes. This could be done, for example, as shown schematically in FIG. 22, by placing a layer of functionalized beads on an inert semi-permeable membrane. The membrane can be made resistant to any adsorption by grafting polymers or by blocking its surface. A layer of magnetic beads could be deposited and held at the bottom by a magnet. Depending on the type of analyte, this could be an ultrafiltration membrane for protein and DNA molecules, or a microfiltration membrane for cells and viruses. In the latter case concentrating of analytes may be performed by filtration or by applying electrical or centrifugal force.

Figure 22:
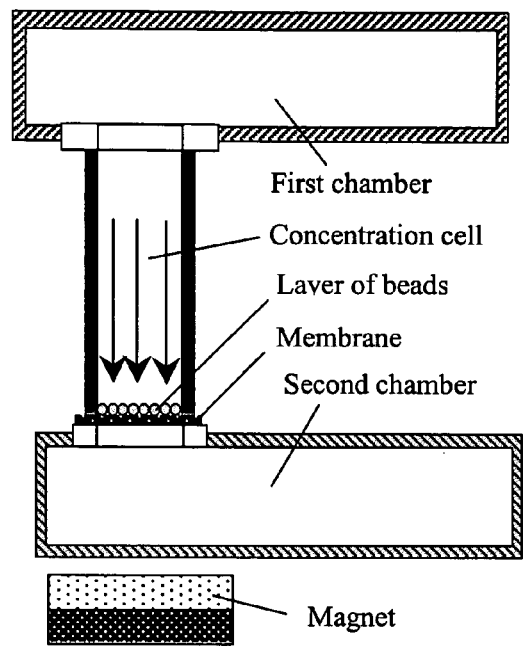
FIG. 22 schematically illustrates use of a layer of functionalized particles on an inert ultra- or micro-filtration membrane to capture analyte (molecules, viruses or cells) actively concentrated in vicinity of the layer.

Using this basic principle different devices for an active assay can be designed to rapidly detect pathogens, such as viruses. A schematic of one such device is presented in FIG. 23. Electro-concentration is performed in a conic intrusion in a polyacrylamide gel (PAAG) plug (420) in a concentration chamber (400), which as illustrated can be an electrophoretic cell (410) that includes an electrode chamber (430). The polyacrylamide gel plug is used as a concentrator and has advantages over the membrane shown in FIG. 22, of being easily formed to have any shape within an electrophoretic cell of any cross-section. A thin flat cell made of two glass plates using two spacer strips (as shown in FIG. 22) is advantageous for heat dissipation upon electrophoretic concentration. The inner surface of the cell can be treated with [γ-(methacryloxy) propyl]-trimethoxysilane (Morozov et al., (1996)) to enable covalent binding of PAAG to the glass surface. A long (20-50 cm) thin capillary represents yet another possible design of the concentration chamber in which analyte can be concentrated up to $\sim10^5$-fold, providing extremely high efficiency in detection of trace amount of viruses, cells and molecules.

In one embodiment, a sample is introduced into the concentration chamber above the semi-permeable membrane, which can be a semi-permeable gel (420), for example by pipetting the sample into the chamber. The sample can be a dilute sample, such as a dilute virus sample. Beads (460) can then be added to the concentration chamber, such as the electrophoretic cell (410) shown in FIG. 23. A current is then applied in the electrophoretic cell to concentrate the viral particles in the sample and the beads (460) to facilitate binding of viral particles, for example, to the beads to result in beads that are coated with analyte on their surface.

Next, the beads with captured viral particles on their surface are moved into a flow-cell (470) that includes a probe array, such as an antibody array (480) on at least a portion of one or both walls. The "rolling stones" method is a preferable technique to be used for methods that use the apparatus shown in FIG. 23. In this example, the beads are moved with a rolling or sliding motion across an immobilized array of probes (480) on an activated membrane. The rolling or sliding motion is provided by liquid flow using a pump (490) to move beads across the activated membrane, and a magnetic force provided by a magnetic (500) to pull beads down to the probe-containing surface of the activated membrane. Accordingly, the suspension of beads with captured analyte on their surface are pumped through the flow cell back and forth using a pump (490), until enough beads with antigens or viruses bound will be tethered to probe spotted on the microarray (480), or until enough images are averaged to obtain a reliable statistics of temporarily tethered beads. The beads are detected on the array using a detection system, for example by detecting light scattering. The detection system includes, for example, a light source (510), and a CCD camera (520) attached to a microscope (530).

The density of beads on each spot gives an estimation for the analyte concentration. To fully use a power of array in parallel analysis, a mixture of beads bearing antibodies against different analytes can be used. Other strategy for parallel analysis of many similar virus strains simultaneously is to coat beads with an antibody which binds all the virus strands. The beads binding different strains can then be sorted on a microarray containing spots of antibodies specific for antigenic determinants unique to each virus strain. It is important that this design does not requires manufacturing microarray on an electrically conductive substrate. Virtually any material (e.g., glass, mica and dielectric polymer films) with a smooth surface can be used to ensure good contact with magnetic beads.

Use of Flow/Electrophoresis to Capture Molecules and Cells on an Active Ultra-Filtration Membrane. Apparatus for Active Detection and Identification of Cells, Cell Fragments and Viruses.

This aspect of the methods and apparatus of the invention combine active collection of large analytes on a membrane capable of selectively capturing these analytes with subsequent detection of immobilized analytes by beads.

The first step, as shown in FIG. 24, includes collection of analytes onto a membrane surface. This can be done using electrophoresis or ultrafiltration. Furthermore, sedimentation is another method that can be used to collect viruses, although this method requires very high speed and expensive centrifuges. For example, the surface is covered with an array of capturing antibodies which hold analytes on the surface while other particles and debris present in the sample are actively removed by reversing field direction or by flow. Viruses can be effectively collected by electrophoresis. For example, adenovirus is negatively charged at pH=7 and its mobility in the capillary electrophoresis reaches $v/E=1.54\times10^{-4}$ cm$^2$V$^{-1}$ sec$^{-1}$ (Mann et al., (2000), Okun et al., (1999)). In an electric field of 300 V/cm, readily obtainable in electrophoretic cells, adenovirus will move with the speed v=0.46 mm/sec and pass 1 mm in 2 sec. Thus, passing sample through a gap, 1 mm high, between two dialysis membranes, 5×5 mm$^2$ one can collect all the virus particles in 1 mL sample in about 1.5 min. This time could be still further reduced by a factor of 3-4 by increasing electric field. This can be achieved by introduction of a cooling system and by desalting of samples. Thus, decreasing the gap between the dialysis membranes and effective mixing of the buffer solutions contacting with both membranes will considerably improve cooling.

Ultrafiltration of sample through a membrane with a surface coated with capturing antibodies presents another method for collection of viruses. As an illustrative example, using a Biomax filter (as advertised by Millipore) one needs 4 min to collect all the particles from a sample, 0.5 mL in the active area of 0.48 cm$^2$. The apparatus can accept both membranes uniformly covered with a single capturing antibody or with an array of spots presenting antibodies with different specificities. The surface is made resistant to nonspecific binding (e.g., by grafting a polymer), to allow easy removal of other particles. To collect most of rare analytes from the sample the capturing procedure is preferably repeated using reversed sedimentation or electrophoretic washing from microfiltration membrane and repeating the active deposition. Such repetition is especially beneficial in the case of arrayed antibodies with different specificities, where only a fraction of surface can catch each particular analyte.

The first stage can also include a separation procedure upon the deposition of analytes. This could be made as shown schematically in FIG. 24. Here a thin laminar jet of a sample solution is subjected to an electric field directed perpendicularly to the flow. Combined action of flow and field will result in deposition of certain viruses or cells in specified areas of active membrane. This procedure increases chances of specific analytes to have access to membrane surface to become captured.

The second step involves detection of the bound analyte with beads using one of the beads detection technique described. For example, the "rolling stones" technique can be used, since it enables a rapid and comprehensive search of the entire membrane surface. Calculations show that a bead, 1 μm in diameter, coated with biospecific molecules bound via a linker, 10 nm long, probes a band, 2b~0.2 μm wide, when rolling. Thus, to scan every location in H=1 mm wide area with a probability of p=90% we need to roll N~~(H/2b)Ln [(100−p)/100]=11,500 beads. Assuming that specific interactions in the contact between bead- and surface-bound reagents are established in a msec time interval, τ, (as between modified tip of AFM and substrate derivatized with antigens and antibodies (Hinterdorfer, 1996)) we estimate that beads should be rolled over the surface with a velocity of $v\sim2b/\tau\sim0.2/10^{-3}=200$ μm/sec. Hence, each bead can scan a trace 1 mm long in a few sec. With $10^6$ beads in 1 mL of solution (a typical 1% stock solution diluted 1:10,000) one needs to have only 2 μl of the solution to probe whole surface even if each bead is used only once. Although relatively crude, the estimates give arguments in favor of feasibility of the device based on this type of detection. Of course, performance of the apparatus and its design will highly depend on successfully developing effective immobilization procedures, and optimizing the biospecific interactions in bead/surface contact.

Use of Soft Beads or Liposomes to Increase Efficiency in Interaction of Molecules in Bead-Surface Contact.

"Soft" beads are advantageous for effective probing surfaces. Grafting of long polymer chains to surface of a solid bead ether by linking of dextran with high molecular mass (500, kD or more) or by in situ synthesis of polymer brushes on bead surface can be used to create soft layer on bead surface. Successive electrostatic layer-by-layer adsorption of positively and negatively charged polymers present another technique to introduce soft layer on bead surface (Lvov et al., 1995; Lowack & Helm, 1998). It is expected that such layering will make the surface of beads both smooth and soft, to increase bead-surface contact area and probability of reaction between molecules tethered to both surfaces. Yet another possible approach for fabrication of soft functionalized beads consists in formation of liposomes with functional molecules immobilized to lipid molecules. Liposomes can be filled with a suspension of magnetic nanoparticles to control their motion with magnetic field.

The following examples are intended to illustrate but not limit the invention.

Example 1

Electrophoretic Acceleration of the Reaction in the Standard Elisa and Suppression of Convection This example illustrates that electrophoretically enhanced ELISA increases the rate of signal formation and provides increased signal levels for very low concentrations of probe.

Electrophoretic Acceleration of the Reaction in the Standard ELISA.

Figure 2:
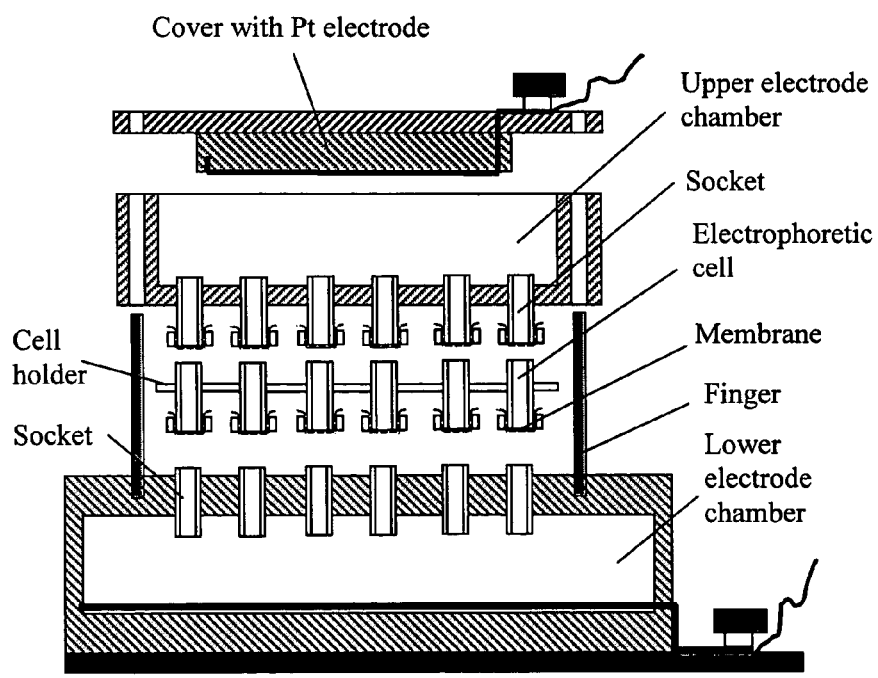
Figure 3:
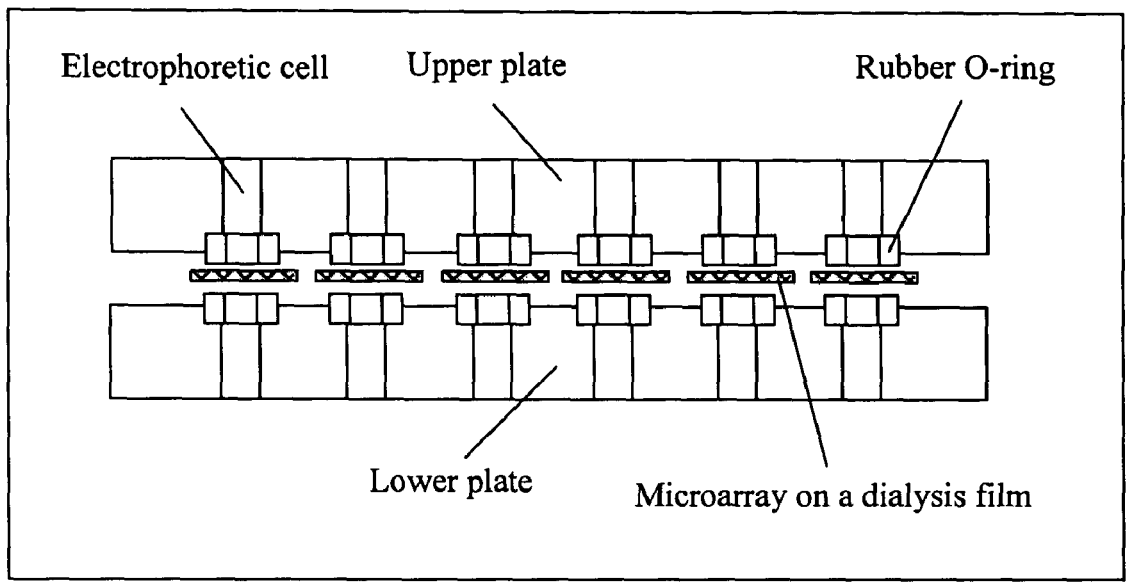
FIG. 3 provides a schematic of electrophoresis cell used in the tests with multi-component antigen microarrays.

A simple device was designed as illustrated schematically in FIG. 2. It includes upper and lower electrode chambers and electrophoretic cells. The lower chamber has an array of open outlets electrically connecting electrophoretic cells with the lower chamber. The upper electrode chamber has also array of outlets. These outlets are covered with a dialysis membrane to prevent leakage of buffer and to allow electric current to pass. Different types of the electrophoretic cells were tested with this basic device. Some of them were made of standard 0.7 mL Eppendorf tubes with their bottom parts and the cover caps cut off. Dialysis film was glued to the upper part of the tube with octylcyanoacrylate glue (World Precision Instruments, Florida, US). The latter glue was chosen to overcome a major drawback of the common cyanoacrylate glue (like the "Crazy glue") consisting in its high volatility and deposition on unprotected film in vicinity of gluing (blooming). Before gluing, tubes were briefly treated in a low-pressure plasma RF-powered discharge as previously described (Morozov et al., 1996) and immediately brought into contact with water. In another cell design dialysis membrane was squeezed between internal wall of Eppendorf tube and a cap. A hole was punched in the cap to allow voltage application. To conveniently operate with cells they were attached to a holder. In yet another cell design pieces of dialysis film were squeezed between two silicon O-ring as illustrated in FIG. 3. This holder was mostly used in microarray-based assay.

The device was tested using the following typical protocol for direct ELISA:

1. Membrane was coated by placing antigen or antibody solution into the electrophoretic cells in concentration of 10-20 μg/ml for 30-60 min in different experiments. To avoid coating cell walls the volume of coating solution was reduced to 30-50 μL.
2. The cells were then rinsed with washing buffer (20 mM TRIS/HCl buffer, pH=7.5, 0.15 NaCl, 0.05% Tween-20) and blocked with 3% dry milk, BSA or casein dissolved in the same buffer lacking Tween-20.
3. Antibody conjugated with alkaline phosphatase was dissolved in a buffer, containing a blocking reagent and the solution was placed in the cells. The conjugate concentrations varied in a wide range. In many cases solutions contained bovine Hb as a blocking and protecting reagent in concentration of 1 mg/mL.
4. Electric field was applied for 6-20 min, voltage varied between 100-550 V, and current—between 0.5 and 3.0 mA/cell. Plus potential was applied to the bottom of the electrode chamber.
5. Voltage was reversed and kept that way for 30 sec.
6. Cells were rinsed with water, then with the washing buffer and filled with pNPP solution.
7. Reaction was allowed to proceed for 10-40 min at room temperature and then was stopped by addition of 0.65 ml of 2N NaOH.
8. Optical density was read at 405 nm using standard optical cell with 1 cm path.

Figure 4:
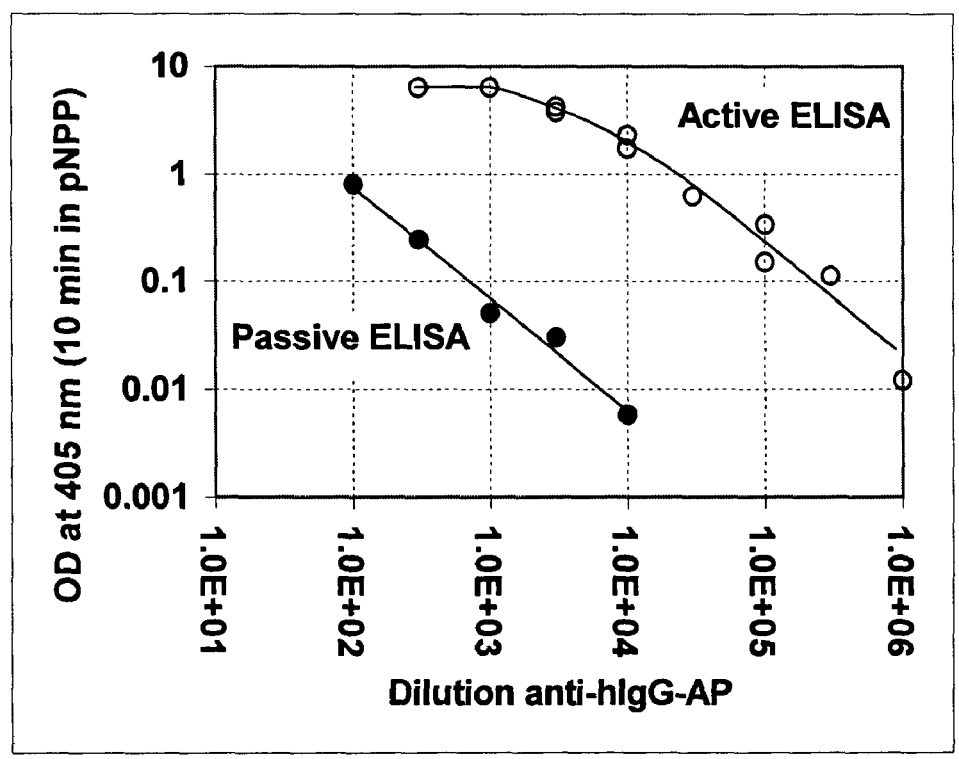
FIG. 4 illustrates acceleration of direct ELISA by electric field. Dialysis membrane (Sigma) was treated for 50 sec in plasma discharge, then 15 min in DDS vapor to make it hydrophobic. Coating was performed from 20 µg/mL of human IgG in 10 mM acetate buffer, pH=5.0 for 1 hour. Electrophoresis of goat anti-hIgG-AP conjugate diluted with 5 mM Gly-Gly buffer, pH=8.5, 0.1% Tween-20, was performed at 1.5 mA/cell (110-200 V) for 10 min. Passive direct ELISA was performed in similar cells for 12 min. All the cells were then washed, filled with 0.2 mL pNPP solution and intensively stirred for 10 min. OD was measured on a microplate reader.

FIG. 4 illustrates the efficiency of active ELISA. It shows that in a very broad range of the conjugate dilutions intensity of ELISA signal (OD) changes in proportion to conjugate dilution and that overall effect of electric field is approximately 300-fold at all the dilutions below saturation levels.

Figure 5:
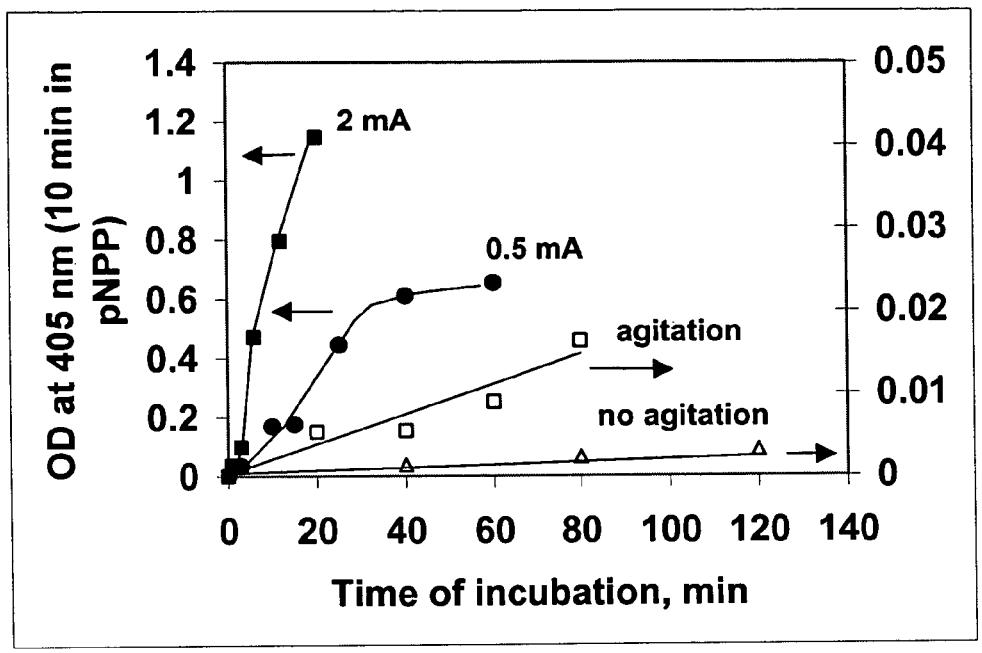
FIG. 5 illustrates the time course of antigen-antibody reaction in active and passive assay. The membrane was treated and coated as described in the legend to FIG. 3. Goat anti-hIgG-AP was diluted 40,000-fold with 5 mM Gly-Gly, pH=8.5, 0.1% Tween-20. 0.2 mL mL of this solution was placed into each EP cell for passive assay (empty triangles for assay without agitation, squares for agitation, 1,500 rpm). Cells to be used in the active assay were filled to the top by 0.46 mL of the same solution and subjected to electrophoresis at 0.5 mA (filled circles) and 2 mA (filled squares). The values presented on the right ordinate are calculated from OD measured after 1 h steering with pNPP in the dark.

FIG. 5 illustrates how formation of antigen-antibody complex (measured as OD in ELISA) is dramatically accelerated upon application of electric field. It is instructive to note, that even intensive stirring accelerates this process only 6-7 fold, according to the data presented in FIG. 5 and the literature data (Franz, & Stegeman, (1991)), whereas application of electric filed increases the rate thousands-fold.

Figure 6:
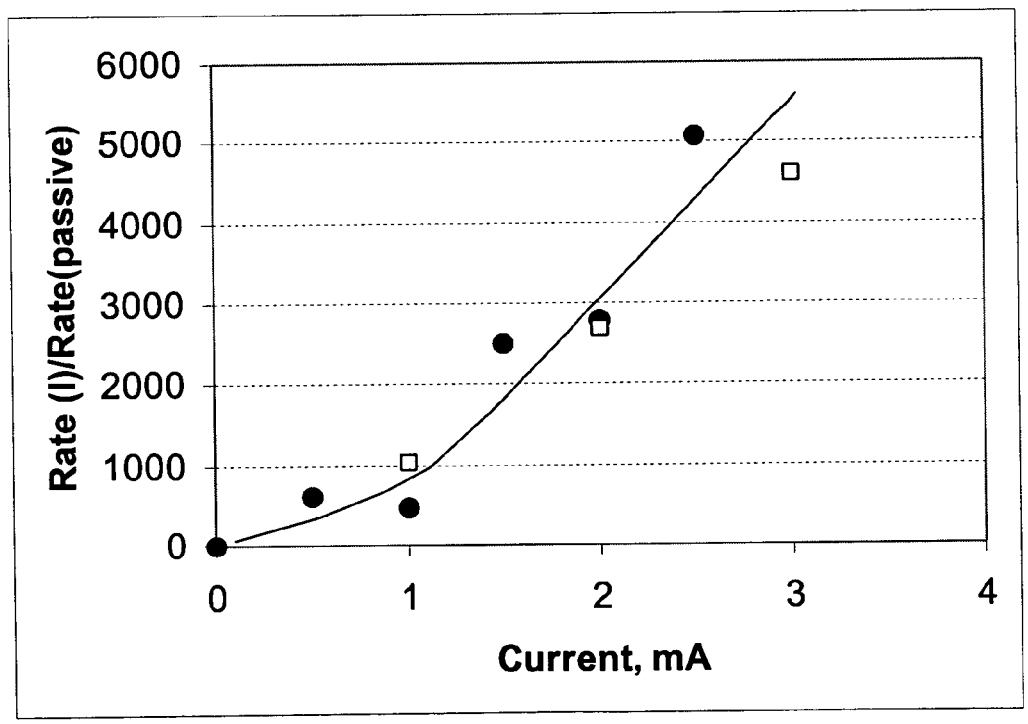
FIG. 6 illustrates the acceleration in formation of antigen-antibody complex with increasing of electric field. Experiment was performed as described in the legend to FIG. 4. Circles for dialysis membrane treated with plasma and DDS with the conjugate dilution of 1:40,000; squares for the conjugate dilution of 1:100,000 and the membrane treated with plasma, followed by exposure to 0.2% PEI solution for 30 min and then to 0.2% of glutaraldehyde in 0.15 M phosphate buffer, pH=7.5 for 10 min.

Increase in the strength of the electric field results in increase of the rate of signal formation in electrophoretically enhanced ELISA, though the dependence is not linear as illustrated in FIG. 6.

Suppression of Convection.

One potential problem upon electrophoretic concentrating proteins in free solution consists of generation of heat inside the cells, which results in heat-induced convection capable of mixing the cell content. Though notable acceleration has been observed even in the presence of convection the latter results in uneven distribution of deposit and preferably should be suppressed. There are several possible ways to suppress convection.

1. Formation of a density gradient by addition of electrically neutral chemicals. Some polymers (dextran, poly(vinylpyrrolidone), glycerol, sucrose and other neutral substances can be used to form density gradient without interfering with the immune reaction.
2. Addition of cross-linked gel beads, like Sephadex, to prevent convection. In this case, inhibition of convection can be combined with protein concentrating and desalting if solute and salt molecules can penetrate the pores within the beads but protein molecules cannot.

3. It has been found in our experiments that a density gradient is automatically formed when 1 mg/ml BSA, dry milk or bovine Hb are added to the solution. Upon electrophoresis at pH=8.5 with plus potential at the lower electrode these proteins migrate to the bottom of the cell forming a stable gradient of density. This gradient effectively prevents convection and allows antibodies to be collected in vicinity of the membrane at the bottom of the cell. Lowering the Hb concentration to 0.1 mg/ml or reversing the sign of the potential to make the protein concentrate at the top of the electrophoretic cell did not result in formation of stable density gradient and a convection was clearly visible.

4. Another type of self-forming density gradient could be established due to polarization of the dialysis membrane under certain conditions. As shown in FIG. 7, electrophoresis through a membrane with positive electrode in the lower electrode chamber results in accumulation of the buffer solution in the vicinity of the membrane, so that conductivity in the lower part of the electrophoretic cell is 10-20 times higher than in the upper part of the cell. In accordance to such distribution of conductivity strength of the electric field and generation of heat is smaller at the bottom of the cell as compared to the top. This result in formation of the temperature gradient inhibiting convection. Under typical experimental conditions the upper part of electrophoretic cells has a temperature that is 2-6° C. higher than that at the cell bottom, which was not different from room temperature. It was found that polarization originates from higher mobility of cations within the dialysis membrane as compared to that of anions, and the polarization-induced temperature gradient could be formed both in weak bases and weak acids as buffers.

Example 2

Device for Performing Electrophoretically Assisted ELISA

This example illustrates a device that can be used to perform an electrophoretically-assisted ELISA assay. An apparatus schematically presented in FIG. 8 allows to simultaneously run 96 independent active assays. Electrophoretic micro-plate was manufactured from a commercial CellScreen plate (Millipore) in which microfilter membranes was removed with a sand paper and replaced with dialysis membranes from regenerated cellulose (Sigma product). The plate was treated in plasma discharge for 50 sec. Dialysis membrane was also treated in plasma discharge for 30-50 sec. Cyanoacrylate glue was evenly distributed over the edges of wells, the membrane was firmly pressed to the wells and allowed to settle for 3-5 min. To prevent deposition of cyanoacrylate vapor onto the membrane, a flow of air was directed into each well via array of sockets prepared from standard 0.2 mL tips. The glued membrane was cut between the wells to reduce tension. Another CellScreen plate was used as an array of sockets to electrically connect the upper chamber with the wells of the electrophoretic plate. A frame was used to press this connection plate to a rubber ring attached to the bottom of the upper electrode chamber (not shown in FIG. 8). To prevent leakage of the buffer each well in the connection plate was either filled with 3-6% gelatin gel (Type A, Sigma) prepared on the electrophoretic buffer, or dialysis membranes were glued to the bottoms of wells as described above. Lower and upper electrode chambers have volume of 0.75 L. A system of parallel platinum wires was used as electrode to evenly distribute current among all the wells. These wires were attached to the cover of the upper chamber and to the bottom of the lower chamber. To protect the electrophoretic plate from accumulation of bubbles generated on the lower electrode system a frame with a dialysis membrane (bubble deflector) was inserted at an angle into the lower chamber as shown in FIG. 8. The frame deflected bubbles to the chamber wall.

One advantage of this design is its compatibility with other standard apparati used in ELISA. Thus, optical density in the wells with membrane bottom were readily measured using a standard automatic microplate reader.

Example 3

Figure 9:
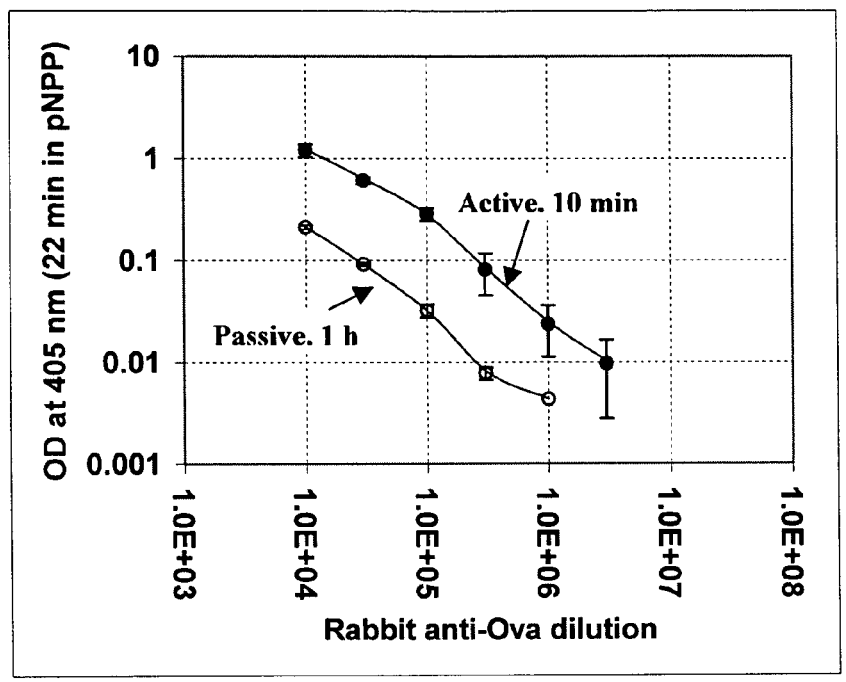
FIG. 9 provides a comparison of signals in EP-assisted ELISA (filled circles) with those in the standard ELISA on a NUNC microplate (empty circles) at different dilutions of primary antibody. Both microplates were coated from 10 μg/mL solution of Ova in 0.15 M carbonate buffer, pH=9.3, at 4° C. overnight. Dialysis membrane at the bottom of the microplate was made hydrophobic in DDS vapor. The EP-assisted binding of primary rabbit anti-Ova was performed from 5 mM Gly-Gly buffer with 0.1% Tween-20 at 2 mA/well for 10 min with stirrer in the lower chamber. Anti-rIgG-AP diluted 20,000-fold was bound under identical EP conditions. In the standard ELISA each binding stage was performed for 1 h from the same antibody solutions in 3% defatted milk in TBS with intensive (~1,500 rpm) agitation. Mean values of controls without the primary antibody are subtracted.

Enhanced Sensitivity in the Electrophoretically Assisted ELISA as Compared to ELISA in Commercial Microplates This example illustrates that electrophoretically-assisted ELISA provides increased sensitivity. In this example electrophoretically-assisted ELISA was performed using the apparatus described in Example 2 and protocol described in the Example 1. FIG. 9 presents a comparison of the active assay with the standard assay on a commercial polystyrene microplate. The data presented in FIG. 9 clearly demonstrate that active ELISA is substantially more sensitive as compared with the standard ELISA performed under the most optimal conditions (long time of coating and reaction, optimal pH and salt composition in the reaction buffer).

Example 4

Electrophoretic Washing

Figure 10:
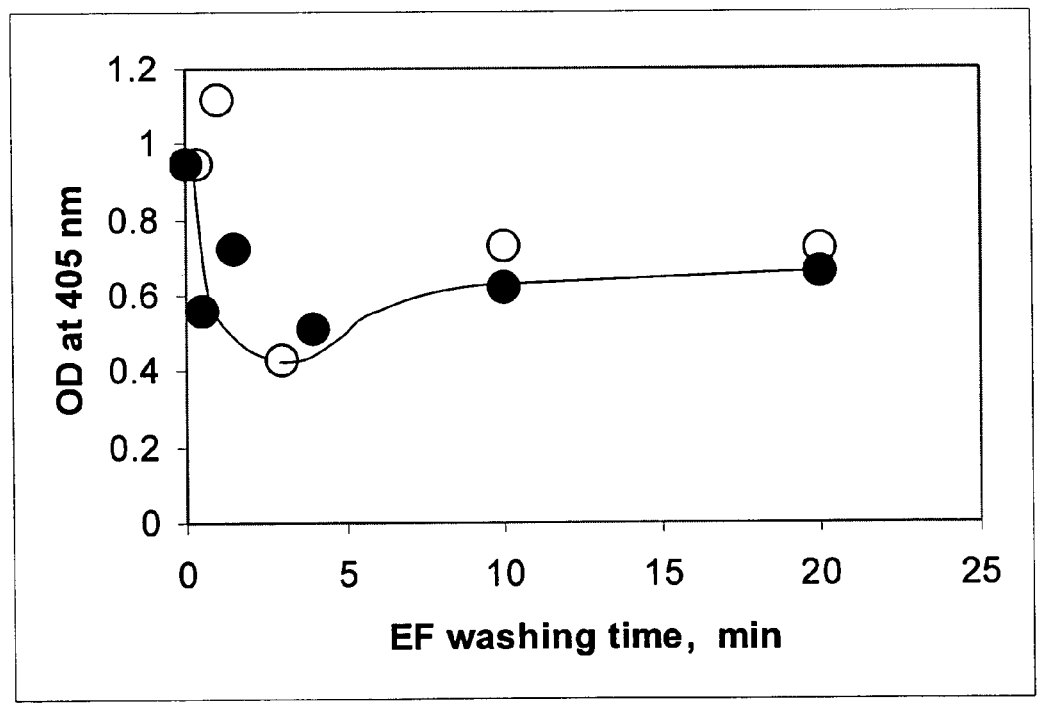
FIG. 10 illustrates the effect of electrophoretic washing on ELISA signal. Results of two independent experiments are presented. Dialysis membrane was glued to electrophoretic cell with a cyanoacrylate glue, coated in 50 μg/mL solution of human IgG in 10 mM borate buffer, pH=8.5, for 5 min and blocked with 3% milk solution. Anti-hIgG-AP conjugate (1:100,000 diluted with the buffer) was electrophoretically bound to IgG for 7 min at 1.5 mA/cell (200 V) then the content of the cell was replaced with the pure borate buffer and the cells were subjected to reversed electric field at 2 mA/cell at 220 V for certain periods. OD was measured after 40 min incubation in pNPP solution

This example illustrates that electrophoretic washing can be used to reduce background levels in an ELISA assay. More specifically, this example illustrates that electric field applied in such a way as to actively remove bound molecules from the surface can reduce the amount of the bound molecules to a certain level, but leaves most of the bound analyte molecules undisturbed. It can, thus, be used to reduce background. As it seen in FIG. 10, electrophoretic washing upon reversal of potential (negative potential at the lower electrode upon washing moves negatively charged antibodies upward from the substrate) quickly reduces the amount of the bound conjugate by 30-40%. Further exposure to field does not produce notable changes, indicating that part of the bound conjugate binds the surface strongly. A slight increase in the OD after 5 min can be attributed to binding of the washed conjugate at the cell walls.

Example 5

Efficiency of Capturing Antibodies in the Active Electrophoretically-Enhances ELISA This example illustrates that an ultimate sensitivity can be rapidly achieved in active assay by enabling collection of nearly all the antibody molecules present in a sample.

Figure 11:
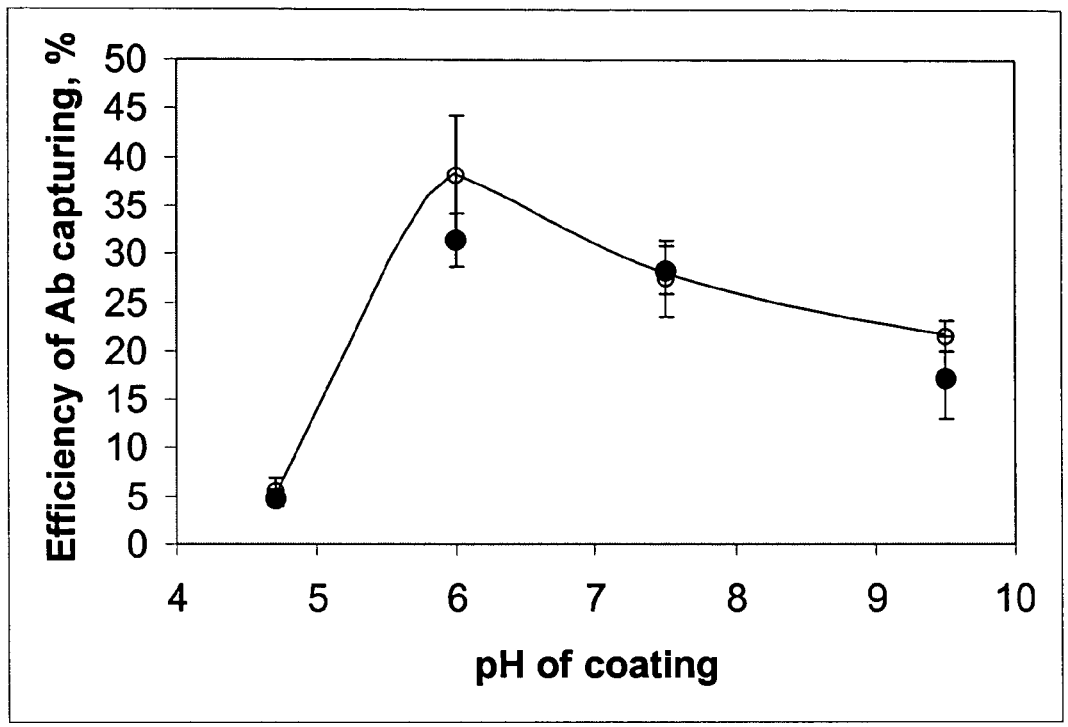
FIG. 11 illustrates the efficiency of capturing antibody in electrophoretically-assisted ELISA. Dialysis membrane was treated in cold plasma, PEI and glutaraldehyde solutions. Dialyzed human IgG was bound to thus activated membrane from 20 μg/mL in different 0.15 M buffers with different pH for 1 h. The membrane was then blocked for 20 min in 3% defatted milk. Anti-hIgG-AP was actively bound from 5 mM Gly-Gly buffer, pH=8.5 with 0.1% Tween-20. Electrophoretic concentration was performed at 1.5 mA/cell (145-200V), for 10 min. Efficiency of conjugate capturing was estimated as ratio of AP activity bound to the membrane to all the AP activity in 0.45 mL of conjugate used to fill the electrophoretic cell.
Figure 12:
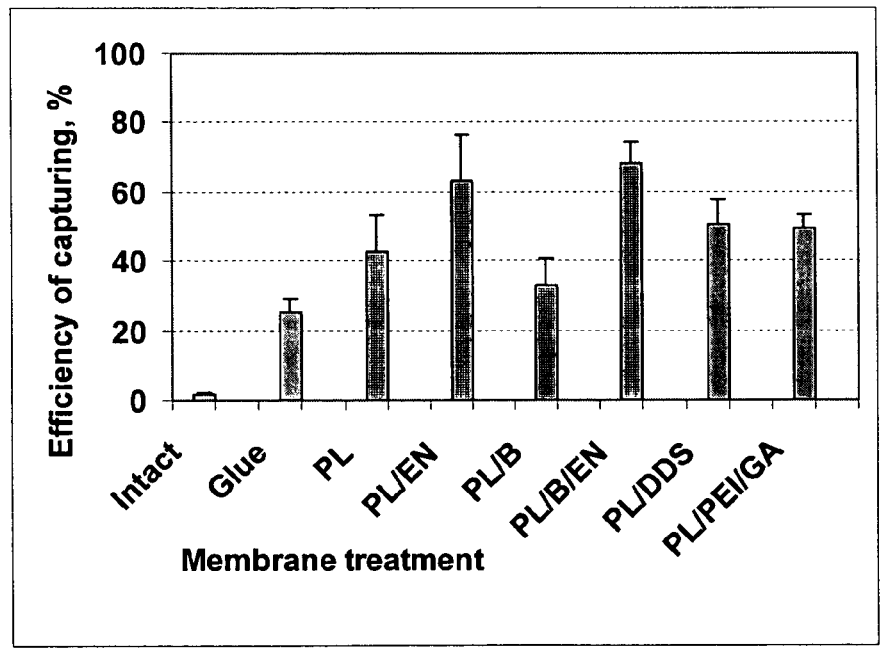
FIG. 12 illustrates the efficiency of antibody capturing in the active immunoassay with different immobilization techniques. Human IgG was immobilized from 20 μg/ml solution in 50 mM phosphate buffer, pH=6.0 for 1 hour. Anti-hIgG-AP was diluted $10^5$-fold with 5 mM Gly-Gly, pH=8.5 with 0.1% Tween-20 and EP was performed with a stirrer in the lower electrode chamber for 10 min at 2 mA/well (plus at the bottom electrode) followed by 30 sec EP washing in the reversed field. The symbols used: Intact, no treatment of membrane; Glue, plasma treated and glued to microplate with a cyanoacrylate; PL, another treatment for 60 sec in plasma after gluing; PL/DDS, PL treated in DDS vapor; PL/B, PL treated in $NaBH_4$; PL/EN, PL treated in EDC/NHS mixture; PL/B/EN, PL treated in $NaBH_4$ and then in EDC/NHS mixture; PL/PEI/GA, PL treated in PEI and then in GA solution. Mean values of controls without coating are subtracted.

In this example total phosphatase activity of diluted anti-hIgG-AP conjugate placed inside electrophoretic cell was measured and compared with the AP activity found after electrophoretically assisted assay bound to dialysis membrane at the bottom of the electrophoretic cell. As shown in FIGS. 11 and 12 efficiency of antibody capturing depends on coating conditions and the membrane pretreatment. In the best conditions 70% of all conjugate molecules placed in the cell were found on the membrane surface after only a 10 min active process, as seen in FIG. 12. Only about 0.04-0.4% is collected under identical conditions without electric field. This example illustrates applicability of active assay to analysis of trace amounts of different analytes (molecules, viruses, cells and cell fragments) in biological samples.

Example 6

Activation of Membranes

This Example illustrates a number of methods that can be used to activate membranes.

Figure 13:
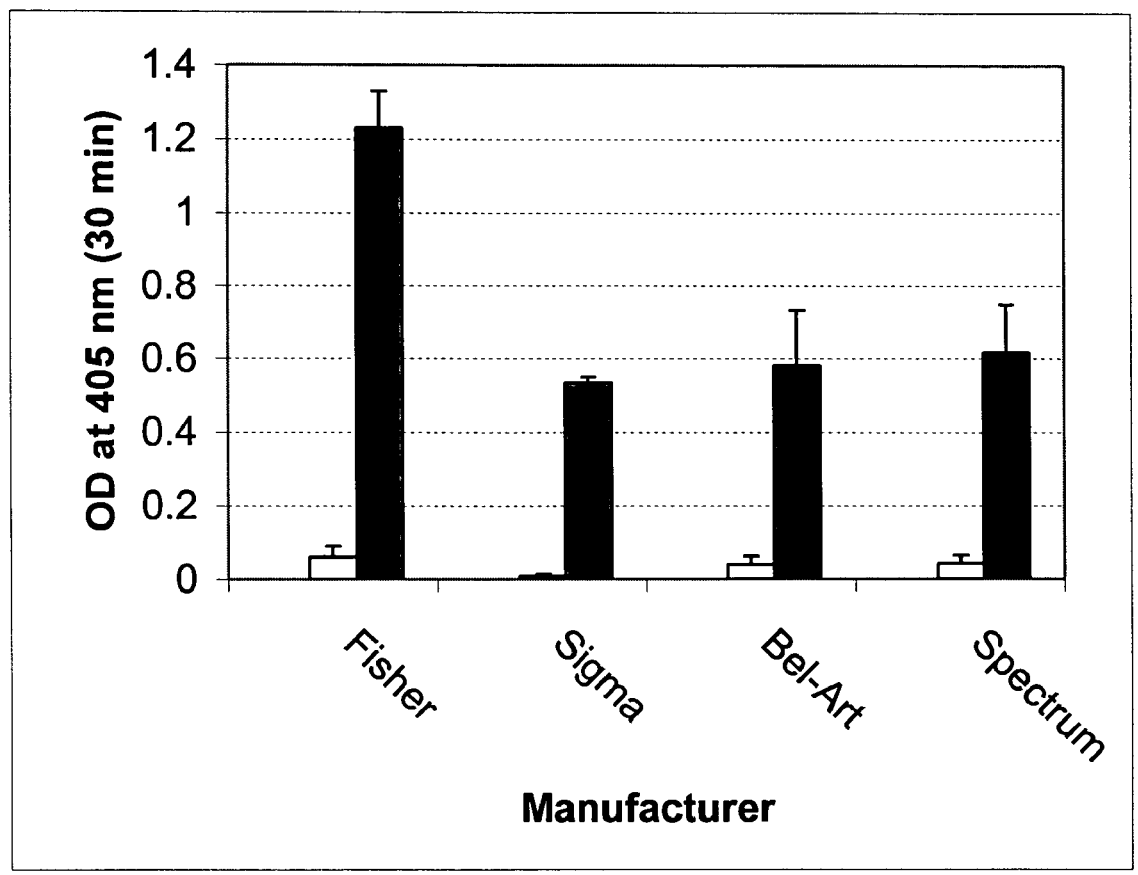
FIG. 13 illustrates the effect of plasma activation on ELISA signal with dialysis membranes obtained from different manufacturers. White bars for OD on initial membranes, gray bars for OD on the same membranes treated in cold air plasma for 20 sec. Coating with h-IgG from 20 μg/mL in 10 MES buffer, pH=6.0, for 1 h. After blocking and washing all the membranes were exposed to anti-hIgG-AP conjugate solution (diluted 1:10,000) for 1 hour with stirring.

Plasma Activation of Semi-Permeable Membrane to be Used in Active Electrophoretically-Assisted Immunoassay Most ultrafiltration membranes are manufactured in such a way as to make them inert with respect of protein binding (see FIG. 13). Such membranes cannot be used as substrate in active immunoassay without some pretreatment procedure directed to enhance their ability to bind antigen or antibody molecules. In this example we present several techniques suitable for activation of membrane surface.

Though many chemical procedures are known for linking protein molecules to cellulose (see G. T. Hermanson (1996)) all these "wet" procedures potentially change the bulk properties (e.g., cut-off parameter) of membranes. This problem may be solved by modification of a surface layer only, which is achieved, for example, in plasma discharge. Cold plasma affects only the top 10 nm depth surface layer on a membrane surface (Martinez, A. J., et al., (2000)) and introduces a rich variety of chemical groups (carbonyl, carboxyl, peroxide and other groups, for oxygen or water plasma) (Nuzzo & Smolinsky (1984); Clement, F., et al., (2002)), which could be used to bind protein and other probe molecules.

Binding with plasma-treated surface of a dialysis membrane from regenerated cellulose (cellophane).

Pieces of dialysis membranes obtained from a number of manufacturers were washed in distilled water for a few minutes, glued to a stainless steel plates with 5% PVP solution and then shortly treated in cold plasma (50 sec, 30 W, discharge in air at reduced pressure), then washed with distilled water and placed into cells. The membrane within the cells were coated with human IgG solution (20 µg of IgG in 10 mM MES buffer, pH=6.0) for 1 hour. After washing and blocking with blocking solution (3% defatted milk, 20 mM TRIS/HCl buffer, pH=7.5, 0.15 NaCl) anti-hIgG-AP conjugate diluted 40,000 times with the blocking solution was placed in the cells and the latter were intensively stirred for 1 hour. The cells were then thoroughly washed and stirred with 0.2 mL of pNPP solution for 30 min. FIG. 13 presents comparison of the ELISA signals obtained on plasma-treated and untreated membranes. It is seen that plasma increases the signal up to 60 times for Sigma membrane which has the lowest initial protein binding.

Figure 14:
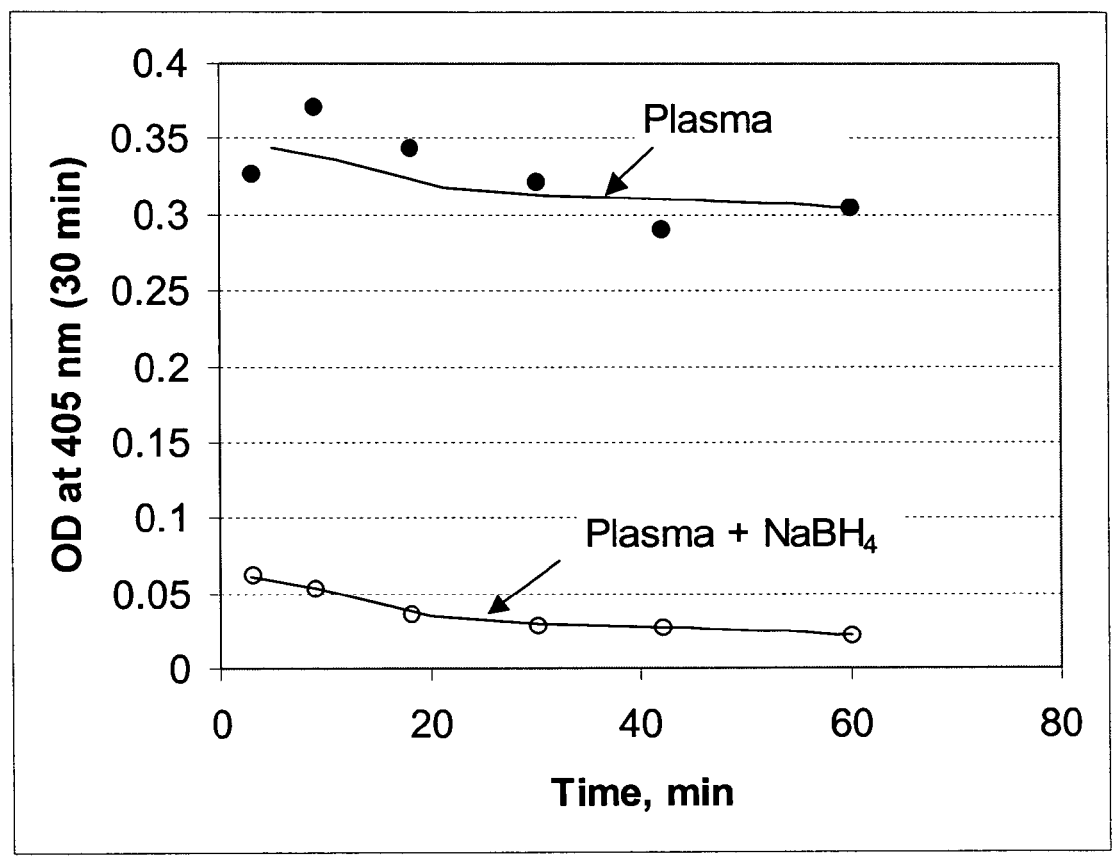
FIG. 14 illustrates strong covalent binding of proteins with a surface of a dialysis membrane treated with cold plasma. Membrane from regenerated cellulose (Sigma) was subjected to plasma for 50 sec and then placed into water. Part of this membrane was then treated in $NaBH_4$ solution (10 mg/mL for 4 hours). Both membranes were then coated with alkaline phosphatase (AP) from 10 μg/mL in 10 mM acetate buffer, pH=5.0, for 1 h. AP activity was measured in electrophoretic cells with the membranes at the bottom as function of washing time. Washing solution (10 mM borate buffer, pH=9.5, 1 M NaCl, 0.05% Tween-20) was changed every 3 min. After washing the membranes were placed into pNPP solution and subjected to intensive stirring for 30 min before measuring OD.

To test stability of protein binding to plasma-treated surface of a dialysis membrane and to reveal chemical character of bonding experiments with alkaline phosphatase (AP) were performed. Coating of plasma-treated membrane was performed from 10 µg/mL solution of AP in 10 mM acetic buffer, pH=5.0 for 1 hour. The phosphatase activity was measured in the above described cells after different number of washings with 10 mM borate buffer, pH=9.5, 1 M NaCl, 0.05% Tween-20. As seen from FIG. 14, coating to the plasma-treated surface results in strong irreversible binding. It is also seen in FIG. 14 that the binding capacity of the plasma-treated surface is reduced many-fold after exposure to a solution of $NaBH_4$ (10 mg/mL in water for 1 hour) and the remaining binding becomes weak and reversible. Since $NaBH_4$ is known for its ability to reduce aldehyde groups we may conclude that these groups are mostly involved in binding proteins to plasma-treated surface, presumably, through formation of Schiff' bonds (Hermanson, 1996).

Hydrophobization of dialysis membrane as a method to enhance protein binding

Hydrophobization of the membrane surface results in a drastic increase in protein binding. This could be achieved either by deposition of octyl cyanoacrylate vapor (data presented in FIG. 10 were obtained on such membranes) or by a treatment with silanes without sacrificing membrane ability to support ionic current. It was found that plasma-treated surface of dialysis membrane can be rapidly made hydrophobic by keeping the membrane in a vapor of dichlorodimethylsilane (DDS). Since this reagent is sensitive to water the procedure is preferable performed in atmosphere of dry nitrogen. Specifically, membrane was placed for 5-15 min into a jar where a flow of nitrogen passed through a vial with DDS was introduced. Data presented in FIGS. 4, 5, 6, 9 are obtained using such membranes.

Other techniques for activation of membrane surface.

Other groups formed in cold plasma on membrane surface can be used to bind probe molecules. Thus, a large density of acid groups is introduced into the surface. Our direct titration revealed that after 30 sec in plasma discharge one acidic group (presumably carboxylic) is introduced per every 8 $A^2$ of surface, making membrane surface negatively charged at neutral and basic pH.

Negative charge of the plasma-treated surface can be exploited to bind proteins using electrostatic interaction either directly or via a polymer carrying positive charge. We found that polyethylenimine (PEI, 70 kD, Sigma product) strongly binds to plasma-treated surface from its 0.2% solution in water, pH=9.2. After activation of PEI amino-groups with glutaraldehyde the surface acquires ability to covalently bind proteins. Data presented in FIG. 11 are obtained on a membrane activated as described. FIG. 12 illustrates comparative efficiencies of different immobilization techniques under slightly acidic coating conditions. It is seen from FIG. 12 that polyethylene/glutaraldehyde activation increases coating as compared to plasma-treated surface.

Figure 17:
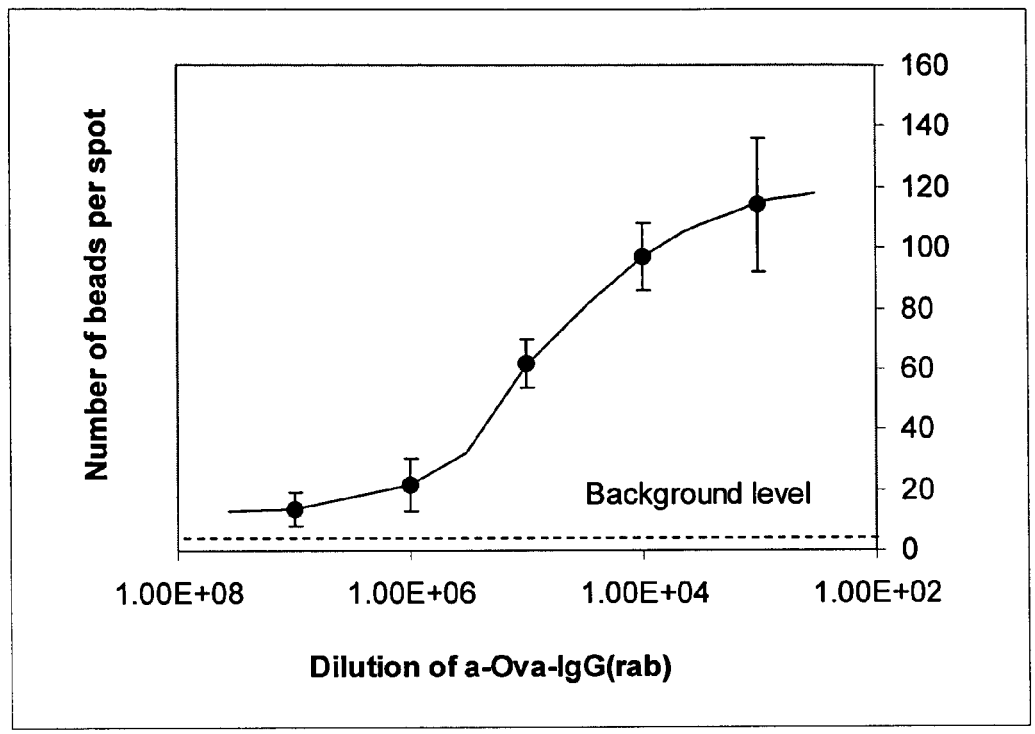
FIG. 17 provides a graph of beads density as a function of antibody concentration. Ovalbumin was arrayed on activated dialysis membrane with subsequent covalent binding. The membrane was treated in plasma discharge for 30 sec, then reacted with adipic acid dihydrazide (2 h in 30 mg/mL of AAD dissolved in 1 M NaCl, pH=5.0) and then overnight with partially oxidized dextran (140 kD, 20% oxidized, dissolved in the same solution). Electrophoretically assisted binding of polyclonal anti-ova-IgG (rabbit) from 10 mM Gly buffer, pH=8.5 for 7 min at a voltage of 300-390 V and current of 0.5 mA/cell. Magnetic beads were applied in 1% BSA solution in 100 mM phosphate buffer, pH=8.0 and were further manipulated as described in the legend to FIG. 14.

It is obvious that a variety of other known techniques based on activation of carboxyl and aldehyde (ketone) groups (Hermanson (1996)) can be used to bind probe molecules to the membrane surface ether directly or via different linkers. Thus, a short-term (7 min) activation of plasma-treated dialysis membrane with a freshly prepared mixture of 0.2 M of 1-ethyl-3-(3-dimethylaminopropyl) carbodiimide (EDC) and 50 mM of N-hydroxysuccinimide (NHS) resulted in 20-30% increase in efficiency of the membrane coating as seen from FIG. 12 (compare "PL" and "PL/EN" bars in this figure). In yet another immobilization technique tested adipic acid dihydrazide was used to bind oxidized dextran linker to plasma-treated surface. Protein arrays fabricated on such a surface displayed a very low background in magnetic bead detection as seen in FIG. 17.

Example 7

Magnetic Bead-Linked Immunoassay. Detection of Interaction Between H-IgG and Protein G by Magnetic Beads Controlled with Magnetic Field This Example illustrates an active magnetic bead-linked immunoassay. One major bottle-neck in the development of express immuno-assay analysis based on ELISA protocol appears the enzyme labeling itself, since time needed to obtain a measurable signal in enzyme reaction becomes excessively long at low analyte concentrations. Several alternative detection techniques have been described in literature. Plasmon resonance is well applicable to detection of antibody-antigen reaction. However, the special substrate (i.e., 50 nm gold layer on an optically flat transparent substrate) used in this method is not compatible with the electrophoretically-enhanced assay.

Magnetic beads first used as a solid phase in the heterogeneous immunoassay (Stannard et al., 1987), were later applied as labels for detection of antibody-antigen reaction. Detection of beads bound to a surface has been performed using SQUID technique (Enupuku et al., 1999), using resonant coil (Richardson et al., (2001)), a force amplified biosensor (Baselt et al., 1997) or directly by counting particles under an optical microscope (Lee et al., 2000). These detection methods are not sensitive enough (e.g., at least $10^3$ particles are required to obtain positive response in the resonant coil of Richardson et al., (2001) or tiresome as in direct counting. The latter technique also meets a difficulty in recognizing magnetic beads among other impurities and defects on the substrate surface.

To overcome this disadvantage we deposited primary antibody in a form of a microarray. Such deposition (i) allows an easy visual recognition of binding and (ii) provides an opportunity to estimate a background (unspecific) binding in the area between the deposited spots.

The following experiment illustrates advantages of combining elecrophoretically enhanced analyte binding with active detection of the bound analyte molecules by magnetic beads covered with proteins specific to the analyte molecules. An antigen microarray was fabricated using electrospray deposition (ESD) technique as described (Avseenko et al., 2002; Avseenko et al., 2001; Morozov & Morozova 1999; Morozov & Morozova 2002). Briefly, a solution of protein antigen (hen egg white lysozyme, 1 mg/mL, 10:1 (W/W) sucrose:protein) was electrosprayed onto a dry dialysis membrane via a polystyrene mask. A piece of a damp dialysis membrane was placed onto a stainless steel plate pre-covered with 5% water solution of PVP (360,000, Sigma) and dried. After deposition microarray on such dry membrane, the membrane was placed for 30 min into 100% humidity. Small microdroplets were formed in humid atmosphere and proteins were immobilized from these droplets to the dialysis membrane. The array was then blocked in 3% dry milk and used in electrophoretic procedure as described above to concentrate antibody on the dialysis membrane.

Figure 15:
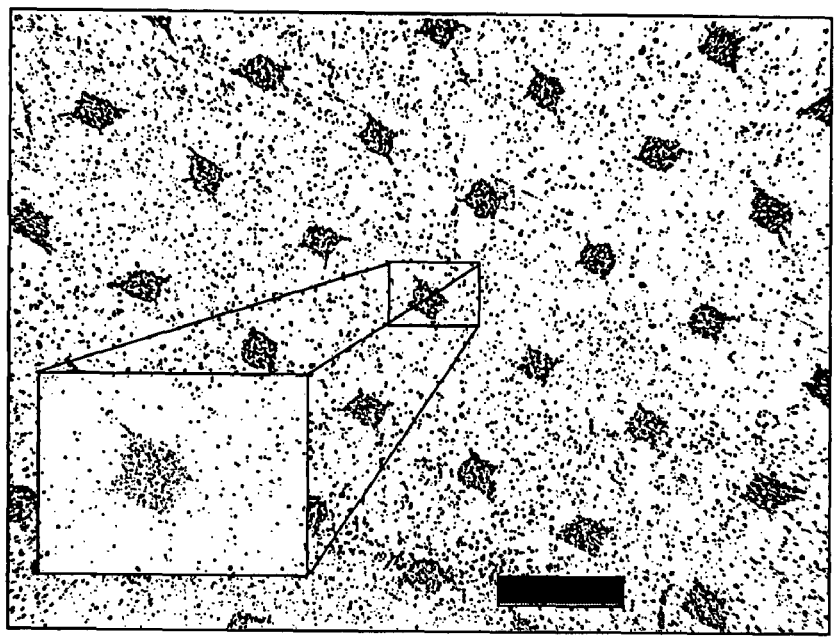
FIG. 15 is a portion of an array of hen egg white lysozyme (HEWL) on dialysis membrane after electrophoretically-enhanced reaction with anti-HEWL IgG and detection of the bound IgG with magnetic beads covered with protein G. HEWL was deposited onto a dry dialysis membrane by electrospray technique from 1 mg/mL solution mixed with 10 fold excess of sucrose. Anti-HEWL polyclonal antibody prepared in rabbit (Chemicon International product) was actively concentrated on the array from 10 mM imidazole buffer, pH=8.5. Electrophoresis was performed for 8 min with 1 mA/cell (400-550 V) followed by a reverse in direction of electric field for 30 sec. Beads were applied onto washed membrane after dilution of stock solution with 0.1% BSA. Magnetic beads were first pulled to the array and then pushed off with a rare-earth micro-magnet. Bar is 150 μm.

After the electrophoretic stage was performed, the array was rinsed with water and brought into contact with a diluted suspension of magnetic beads coated with protein G (1 micron in diameter, Biolabs, New England, type S1430S). Beads were pressed against the surface by approaching a rare-earth permanent magnet to the bottom of the cell. Then another magnet with a sharp magnetic concentrator was approached from above to touch the solution over the array. Upon removal of free magnetic particles from the surface, a lattice of spots marked with bound beads appeared immediately. It was found that spot detection by beads is well repeatable. After the pattern is washed with a strong jet of buffer solution the procedure of detection could be repeated producing the pattern of the same quality. The pattern was well preserved by slow drying the dialysis film soaked in 1% BSA, PVP or other inert polymer. An image of the lattice is presented in FIG. 15.

Figure 16:
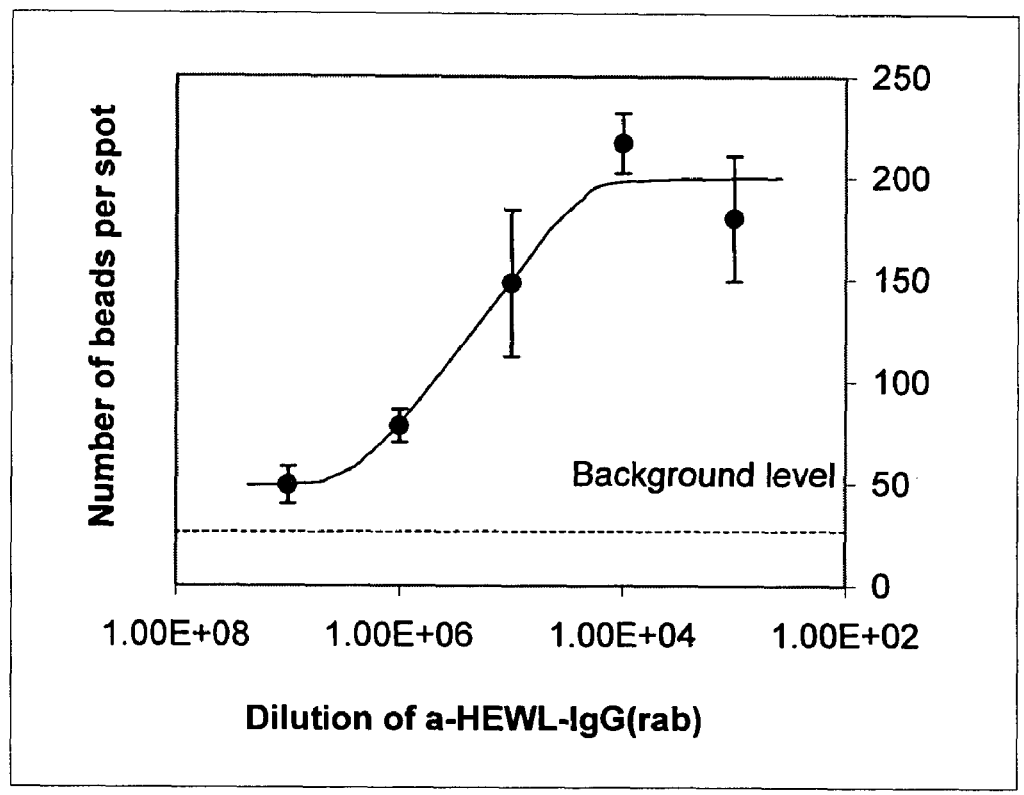
FIG. 16 is a graph showing the average number of magnetic beads in HEWL spots as a function of antibody concentration. Beads remained in spots were counted in randomly 5 chosen spots in each array and averaged. Other conditions are described in the legend to FIG. 14.

The density of magnetic beads in the spots showed notable changes with antibody concentration. FIG. 16 shows how the average number of particles in square spots 30-40 microns changes at different concentrations of anti-HEWL antibody. This example shows, that direct counting of particles or measuring any density-dependent physical characteristics (e.g., light scattering, fluorescence) could be used to estimate the concentration of the analyte molecules in solution.

FIG. 17 presents another example of density of tethered beads as a function of antibody concentration in solution subjected to electrophoretic process. In contrast to the HEWL array described above, an ovalbumin array in this example was covalently linked to the surface of the dialysis membrane via a long inert polymer linker, which also protected the surface from unspecific binding of both antibodies and beads themselves. As a result of this background level is notably (10 times) lower than in HEWL array in which lysozyme molecules were bound to unmodified dialysis membrane.

In another experiment, the same ovalbumin array detection was performed with different magnetic particles ((Sphero™, 1.3 μm in diameter) functionalized with streptavidin. Before detection these magnetic beads were further functionalized with biotinilated anti-rIgG. Density of the beads within the spots notably exceeded those outside the spots even at anti-Ova-IgG dilution as high as 1:$10^7$. No lattice was observed in control experiments when biotinilated antibody against RNAse was bound to beads and when anti-Ova-IgG on bead surface was saturated by Ova in solution before detection on the array. This experiment shows that a great number different functionalities can be introduced into the same beads without sacrificing the active assay sensitivity.

In yet another experiment beads covered with a-rIgG were placed at the bottom of electrophoretic cells and covered with solutions of rabbit anti-Ova-IgG in different dilutions. After EP the beads were collected, washed and used to detect ovalbumin arrayed on a dialysis membrane. Visible lattice was observed at dilution of anti-Ova-IgG up to 1: $10^4$. This experiment proves the feasibility of detection techniques schematized in FIGS. 22 and 23.

Combining electric and magnetic forces in an assay, provide a number of advantages:
1. The assay is far more rapid as compared with the standard ELISA since it eliminates the need for two time-consuming steps: binding of enzyme-labeled conjugate and exposure to substrate solution to reveal the bound conjugate.
2. Beads detection is repeatable, i.e., signal can be re-measured with many different beads.
3. Background and discrimination between specifically and non-specifically bound beads can be controlled by applying force to pull beads off the surface. This can reduce background dramatically (Lee et al., 2000).

Effect of pressing beads to surface.

It was noted in these experiments that pressing magnetic beads to the substrate surface with magnetic field increases the contrast and sensitivity of the detection. This may be explained by increase in the contact area between the bead and surface under this condition. Increase in the contact area will obviously increase the probability of establishing specific interactions between antigens and antibodies bound to the beads and substrate surface. Excessive pressure, however, resulted in formation of strong unspecific contacts.

Example 8

Figure 18:
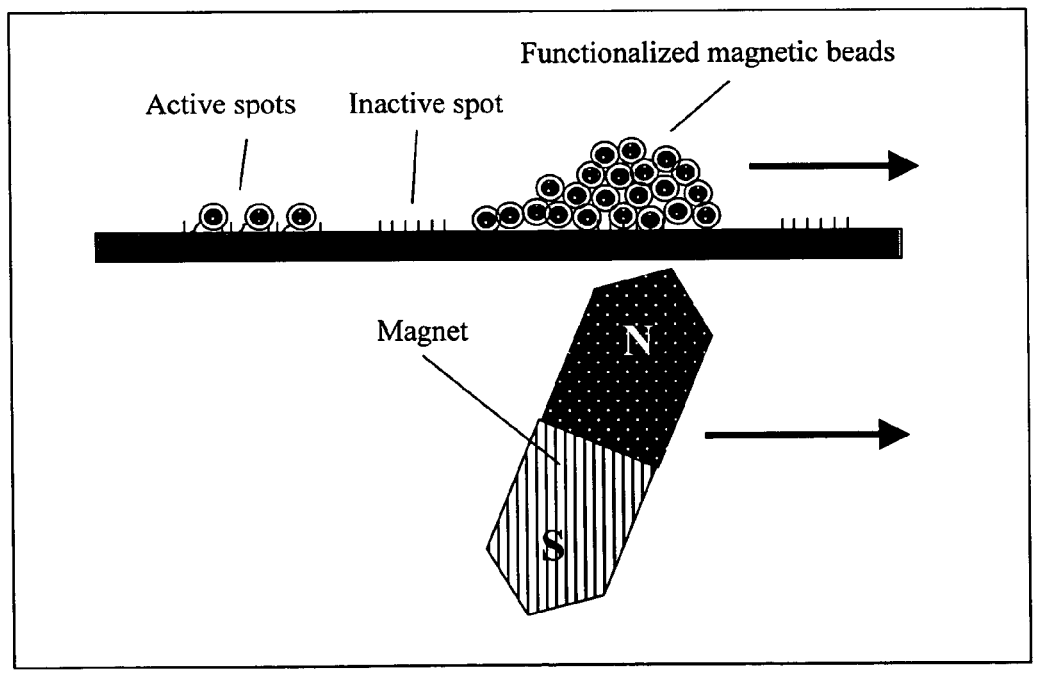
FIG. 18 provides a schematic of "Xerox" process in detection of immune reaction on microarray with magnetic particles pulled over a microarray surface.

Combining of Beads Binding and their Washing in One Process. A "Xerox-Like" Detection Procedure The following example illustrates a method for exposing functionalized magnetic beads to active spots on a microarray. As a part of efforts in design of a device based on detection of immune reaction with magnetic beads different procedures of applying and removing magnetic particles from an immuno-array have been tested. It was found that a lattice could be revealed in a process schematically illustrated in FIG. 18. This process started with the approach of a tip of a magnet concentrator from underneath a microarray. This resulted in formation of a stack of magnetic beads on the membrane above the tip. The tip was then slowly moved under the membrane, pulling the stack over the microarray. A clear array of spots marked with bound beads was observed on the track of the stack. The process of such "Xerox-like" detection takes only a few seconds and provides a basis for development of an express immunoassay procedure which combines electrophoresis transport of analytes to an array on a dialysis membrane and detection of the bound analytes with magnetic beads.

Example 9

Detection of H-IgG Binding to G Protein-Coated Beads Using Centrifugal Forces

The present Example illustrates the use of gravitational force for an active bead assay. Heavy magnetic beads (density of $Fe_3O_4$ is 5 g/cm$^3$) can be easily transported to and from any surface using centrifugal force. We tested the possibility of using centrifugal forces to transport these particles to and from a microarray deposited on a dialysis membrane. A microarray of human IgG was fabricated by electrospray and small discs were cut off and placed face up in 1.5 mL Eppendorf tubes. The tubes were filled with a highly diluted suspension of magnetic beads, 1 micron in diameter, functionalized with protein G. Tubes were placed in a bench centrifuge capable of providing acceleration up to 2,000 g. Centrifugation was continued for 30 sec then discs were rotated to a position face down and tubes were centrifuged again for 30 sec. After withdrawn from the tubes, an array of spots covered with bound beads were observed, very similar to those presented in FIG. 15.

This example shows that gravitational forces could also be effectively used to manipulate non-magnetic beads. Advantage of these forces includes a wide choice of commercial beads and the possibility of using fluorescent beads. A gravitationally controlled immunoassay may also be used to manipulate natural aggregates and whole organisms like bacteria, viruses, cell fragments.

Yet additional advantage of centrifugal forces over the magnetic ones include the following. Upon application of magnetic field ferromagnetic particles turn into micromagnets. These micromagnets attract each other and tend to form aggregates. Such aggregation may present a problem in precise manipulations with magnetic beads. Gravitational forces do not have such a drawback.

Example 10

Active Immuno-Assay with a Multi-Component Antigen Microarray

Figure 19:
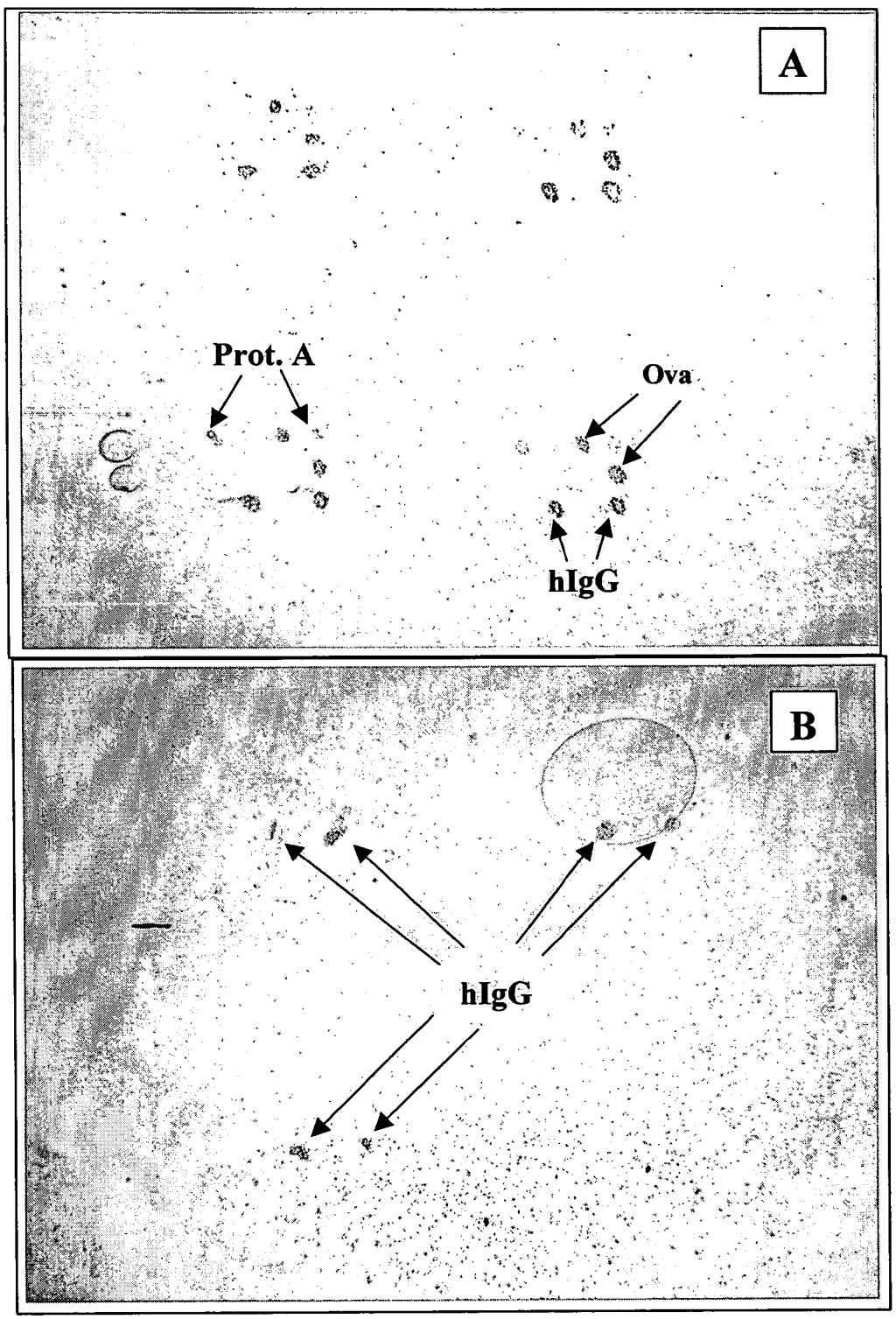
FIGS. 19A-19B illustrate the pattern of magnetic beads bound to dialysis membrane with four microarrays each containing 6 different proteins after electrophoretic application of anti-Ova-IgG polyclonal from rabbit (Panel A) and without antibody application (Panel B). Magnetic beads are covered with protein G.

This example illustrates advantages of combining electrophoretically-assisted immune reaction on a multi-antigen array with magnetic detection of bound antibodies. Arrays of different proteins were electrospray deposited as previously described (Morozov & Morozova 1999; Avseenko et al., 2001) onto a dry dialysis film glued to a glass surface with 5% PVP. 1,200 identical chips were manufactured with 30-50 µm spots and 150 µm between spots. The proteins were adsorbed to the dialysis surface by exposing the film to 100% humidity for 30 min, the surface was then blocked with a solution containing 3% dry milk and stored at −20° C. in 50% glycerol solution prepared in the blocking solution. Small pieces containing 6-8 arrays were cut from the film and squeezed between two plastic holders, forming a system of electrophoretic cells as shown schematically in FIG. 3. Specific antibodies from rabbit (Chemicon International) were diluted 1:10$^4$ with 1 mg/ml of bovine Hb on 10 mM imidazole buffer, pH=8.6, and placed into the upper holes of the cells. Holes below the membranes were filled with the buffer. The holder was then placed between the electrode chambers shown schematically in FIG. 2. Electrophoretic transport of antibodies was performed at 400 V with a current, 0.5 mA per cell for 4 min. The membranes were rinsed with water, washed 3 times with the washing solution (20 mM TRIS/HCl buffer, pH=7.5 with 0.15 NaCl and 0.01% Tween-20). Stock solution of magnetic beads was diluted 250 times with 1% BSA and applied onto the microarrays. Beads were shortly pressed against the surface by approaching a rare-earth magnet from the bottom, then free and weakly bound beads were removed by approaching the tip of the magnet concentrator to the top of the device. Excess BSA solution was then gently sucked off and the membranes were allowed to dry on a slide surface. Distribution of beads was easily seen under a dark-field illumination. The illustration presented in FIG. 19 clearly shows that pattern of bound beads well matches the position of antigen spots.

Example 11

"Rolling Stones" Technique of Beads Detection

Figure 20:
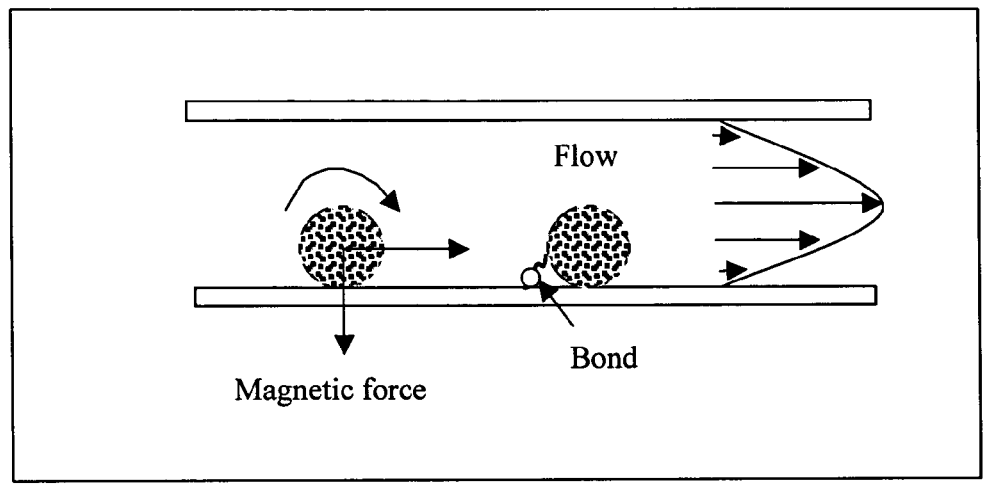
FIG. 20 provides a schematic of the "rolling beads" experimental set.

This example presents an important modification of the active procedures in which a dynamic active search for specific interactions is performed over the solid substrate. Magnetic beads were pressed against a chip surface by an uneven magnetic field and forced to roll or slide over the chip surface by liquid flow at the same time, as shown schematically in FIG. 20. Each particle is, thus, probing not a single contact area, as in the previously described techniques, but rather a track. A piece of dialysis membrane with an IgG array on it was placed onto a glass plate and attached to a flow chamber, 4 mm wide and 30 µm high, made of a rubber plastic. Stock solution of magnetic beads (S 1430S, Biolabs, New England) coated with protein G was diluted 1,000 fold with 0.5% casein solution on 20 mM TRIS/HCl buffer, pH 7.5 with 0.15 NaCl. Approaching a small rare-earth magnet to the bottom of the cell at slow flow resulted in a rapid (in a few seconds) formation of a visible lattice of spots marked by the bound magnetic particles. No beads were bound outside of the spots, proving that beads arrest was due to specific interactions. No such lattice appeared after few minutes in flow when no magnet was applied or when magnet was applied from the top to attract particles to the upper plastic plate of the flow chamber. Thus, rolling over the microarray surface highly promotes interaction of beads with antibody molecules bound to the surface.

It was found that after binding of a certain amount of beads to a spot, this spot showed a marked tendency to attract and bind additional beads from solution. This effect can be attributed to known phenomena of aggregation of magnetic beads in magnetic field with beads bound to spots acting as seeds for such aggregation. Such seeded aggregation provides the opportunity for large signal multiplication and, hence, for increased assay sensitivity.

Increase in the flow rate to about 0.1 mL/sec which corresponds to a mean velocity of 0.8 m/s results in complete removal of beads from the surface. Estimation of forces acting on a particle, 1 μm in diameter attached to a flat wall and subjected to such flow was made using Eqn. 15 to give 1.3 nN. This force considerably exceeds maximum force necessary to break a single antigen-antibody bond (0.04-0.25 nN). Thus, beads in our experiments are bound to the surface via multiple specific bonds. In contrast to the Lee et al. (2000) approach which uses weak magnetic forces, forces generated by flow in our system provide more opportunities in discriminating specific and non-specific bonds.

After cleaning the surface by fast flow the beads could be bound to the same IgG spots again in slow or moderate flow. Such process was repeated 6 times without a notable deterioration of the binding pattern. Thus, a detection procedure based on rolling stones is readily reversible, providing a property that could be used to eliminate errors.

With the magnetic and flow forces well adjusted to the bond rupture forces, this technique allows rapid detection of rare interactions. For example, 10-100 viruses from a water sample can all be moved to an active surface using electrophoretic process and bound there. Their presence and position on the surface can then be detected by rolling particles.

Other combinations of forces can be used to organize the "rolling" process. Thus, an electric field can be used to press charged beads to a substrate surface. Charging the surface with the opposite charge and reducing salt concentration in solution may be used to hold particles attached to the surface while letting them roll in flow or under action of any other force directed along the surface. Beads can also be pressed to the surface by centrifugal forces and moved parallel to the plane using flow, magnetic or electric forces.

Example 12

Disposable Flow Chip with Active Magnetic Detection

The present Example illustrates using a disposable flow chip with a magnetic detection method. A schematic of a simple disposable analytical unit is presented in FIG. 21. Proteins are arrayed on one wall of a chamber composed of two surfaces separated by a thin gap. Surfaces are hydrophilic enough so that gap is filled with sample by capillary forces. A piece of Whatman paper at one end of the gap is used to adsorb solution after it passed through the chamber. On the other side of the gap a small closed compartment is made of plastic, which contains dry suspension of functionalized magnetic beads. A means holds a magnet under the protein array and allows removal of the magnet upon reading the result.

The device is operated as follows. First, sample solution containing primary antibody (e.g., patient blood) is applied to the open end of the gap and allowed to fill the gap. After exposure to primary antibody the chamber is washed with buffer, then the compartment containing magnetic beads is opened, an appropriate amount of buffer is placed in the compartment (box-270 in the FIG. 21) and the suspension of magnetic beads is allowed to penetrate inside the chamber. In the presence of a magnet underneath the array, magnetic beads roll or slide without rotation over the array surface until they become tethered over spots.

To test the unit, ovalbumin was ES deposited on plasma-treated dialysis membrane (Serva, Heidelberg, Germany) glued to a glass slide with 5% gelatin A. After deposition the array was placed for 30 min into 100% humidity created with 10 mM acetic buffer, pH=5.1. The array was blocked with 2% BSA dissolved in 20 mM TRIS/HCl buffer, pH=7.5, containing 0.15 M NaCl. The excess of the buffer was blown by air jet and the array was quickly dried in a stream of air. The flow cell was assembled as described above (see FIG. 21). 50 μL of a solution containing 10% (V/V) rabbit serum and 1% of anti-Ova-IgG prepared in rabbit (Chemicon Intl. Product) was placed into the open part of the gap and allowed to penetrate inside by capillary forces. After 2 min the flow chamber was washed with the buffer, and 100 μL of a suspension of magnetic beads functionalized with protein G (stock solution was diluted 1:200 with 2% BSA) was placed to the open end of the gap, while having a magnet underneath the array. Direct observation under a low-power stereo microscope revealed appearance of lattice, similar to those presented in FIG. 15 as soon as the suspension reached the array. Another control chip was identically treated except for lack of anti-Ova-IgG in the first solution. No lattice of captured beads was observed indicating that the beads bind spots specifically via captured primary antibodies.

A common microscope equipped with a dark-field condenser allowed imaging individual tethered beads. A simple microscope with a dark-field illumination and a magnifier could be used as an inexpensive means to allow semi-quantitative reading of the disposable chip. Density of beads within spot area could also be quantified using other physical characteristics which depend upon density of tethered beads: (i) by measuring overall intensity of light scattered from beads covering spot; (ii) by employing florescent magnetic beads and measuring intensity of fluorescence; (iii) by a magnetic head similar to those used in magnetic tape recorders; (v) by a micro inductive coil, scanned over the array surface.

REFERENCES

1. Avseenko, N. V., Morozova, T. Ya., Ataullakhanov, F. I., Morozov, V. N. (2002) Immunoassay with multicomponent protein microarrays fabricated by electrospray deposition. *Anal. Chem.*, 74, 927-933.
2. Avseenko, N. V., Morozova, T. Ya., Ataullakhanov, F. I., Morozov, V. N. (2001) Immobilization of proteins in immunochemical microarrays fabricated by electrospray deposition. *Anal. Chem.*, 73, 6047-6052.
3. Balcells, M., Klee, D., Fabry, M., Höcker, H. (1999) Quantitative assessment of protein adsorption by combination of the enzyme-linked immunosorbent assay with radioisotope-based studies. *J. Colloid Interface Sci.* 220, 198-204.
4. Baltz, M., Cone, R. A., (1990) The strength of non-covalent biological bonds and adhesion by multiple independent bonds. *J. Theor. Biol.* 142, 163-178.
5. Baselt, D. R., Lee G. U., Hansen, K. M., Chrisey, L. A., Colton, R. J. (1997) A high-sensitivity micromachined biosensor. *Proc. IEEE* 85, 672-680.
6. Baselt, D. R., Lee, G. U., Natesan, M., Metzger, S. W., Sheehan, P. E., Colton, R. J. (1998) A biosensor based on magnetoresistance technology. Biosensors & Bioelectronics 13, 731-739.
7. Bongrand, P. (1999) Ligand-receptor Interactions. *Rep. Progr. Phys.* 62, 921-968.
8. Boumgartner, W., Hinterdorfer, P., Ness, W., Raab, A., Vestweber, D., Schindler, H., Dreckhahn, D. (2000) *Proc. Natl. Acad. Sci. USA,* 97, 4005-4010.
9. Chapman, R. G., Ostuni, E., Takayama, S., Holmlin, R. E., Yan, L., Whitesides G. M. (2000) Surveying for surfaces that resist the adsorption of proteins. *J. Am. Chem. Soc.* 122, 8303-8304.

10. Chen, C. C., Dense, J. B., Warren, J. C. Crystallization of human placental estradiol 17β-dehydrogenase. *J. Biol. Chem.* 251, 3700-3705 (1976)
11. Chen. S., Alon, R., Fuhlbrigge, R. C., Springer, T. A. (1997) Rolling and transient tethering of leukocytes on antibodies reveal specializations of selecting. *Proc. Natl. Acad. Sci. USA,* 94, 3172-3177.
12. Clement, F., Held, B., Soulem, N., Guimon, C. (2002) XPS analysis of polystyrene thin films treated under DC pulsed discharges conditions in nitrogen, oxygen and oxygen-argon mixtures. *Eur. Phys. J AP* 18, 135-151.
13. Enupuku, K., Minotani, T., Gima, T., Kuroki, Y., Yamashita, M., Katakura, M., et al., (1999) Detection of magnetic nanoparticles with superconducting quantum interference device (SQUID) magnetometer and application to immunoassay. *Jap. J. Appl. Phys.,* 38, L1102-L1105.
14. Essevaz-Roulet, B., Bockelmann, U., Heslot, F. (1997) Mechanical separation of the complementary strands of DNA. *Proc. Natl. Acad. Sci. USA,* 94, 11935-11940.
15. Franz, B., Stegeman M. The kinetics of solid-phase microtiter immuoassay. In *Immunochemistry of Solid-Phase Immuonassay.* Ed. J. E. Butler, CRC Press, Boca Raton, Boston, London, 1991, pp. 277-283.
16. Hermanson, G. E. *Bioconjugate Techniques.* Academic Press, San Diego, New York, Boston, 1996.
17. Hinterdorfer, P., Baumgartner, W., Gruber, H. J., Schilcher, K., Schindler, H. (1996) Detection and localization of individual antibody-antigen recognition events by atomic force microscopy. *Proc. Natl. Acad. Sci. USA* 93, 3477-3481.
18. Kala, M. Bajaj, K., Sinha, S. (1997) Magnetic bead enzyme-linked immunosorbent assay (ELISA) detects antigen-specific binding by phage-displayed scFv antibodies that are not detected with conventional ELISA. *Anal. Biochem,* 254, 263-266.
19. Kishino, A., & Yanagida, T. (1988) *Nature,* 334, 74-76.
20. Kritz, K., Gehrke, J., Kriz, D. (1998) Advancements toward magneto assay. *Biosensors & Bioelectronics* 13, 817-823.
21. Kwong, D., Tees, D. J., GoldsmithH. L., (1996) *Biophys. J.,* 71, 1115-1112
22. Lee, G. U., Metzger, S., Natesan, M., Yanavich, C., Dufrene, Y. F. (2000) Implementation of force differentiation in the immunoassay. *Anal. Biochem.,* 287, 261-271.
23. Lowack, K., Helm, C. A. (1998) Molecular mechanism controlling the self-assembly process of polyelectrolyte multilayers. *Macromolecules,* 31, 823-833).
24. Lvov, Y., Ariga, K., Kunitake, T., (1995) Assembly of multicomponent protein films by means of electrostatic layer-by-layer adsorption. *J. Am. Chem. Soc.* 117, 6117-6123.
25. Ludwig, M., Dettmann, W., Gaub, H. E. (1997) Atomic force microscope imaging contrast based on molecular recognition. *Biophys. J.* 72, 445-448.
26. Luthi, Y., Ricka, J., Borkovec, M. (1998) Colloidal particles at water-glass interface: deposition kinetics and surface heterogeneity. *J. Colloid Interface Sci.* 206, 314-321.
27. Mammen, M., Choi, S. K., Whitesides, G. M. (1998) Polyvalent interactions in biological systems: Implication for design and use of multivalent ligands and inhibitors. *Angew. Chem. Int. Ed.* 37, 2754-2794.)
28. Mann, B., Traina, J. A., Soderblom, C. et al., (2000) Capillary zone electrophoresis of recombinant adenovirus. *J. Chromatogr. A,* 895, 329-337
29. Martinez, A. J., Manolache, S., Gonzales, V., Young, R. A., Denes, F. (2000). Immobilized biomolecules on plasma functionalized cellophane. I. Covalently attached a-chymotrypsin. *J. Biomater. Sci. Polymer Edn.* 11, 415-438.
30. Medvedev N. N., Dynamics and cellular effect in Lennard-Jones liquid. *Zh. Phys. Khimii,* 1992, 66(1), p. 152-154,
31. Morozov V. N., Morozova T. Ya. (1992) Mechanical detection of interaction of small specific ligands with proteins and DNA in cross-linked samples. *Analytical Biochem.,* 201, 68-79.
32. Morozov V. N., Morozova T. Ya., Hiort C., Schwartz D. C. (1996) New polyacrylamide gel-based method of sample preparation for optical microscopy: Immobilization of DNA molecules for optical mapping.—*J. Microscopy,* 183, 205-214.
33. Morozov, V. N., Morozova, T. Ya. (1999) Electrospray deposition as a method for mass fabrication of mono- and multi-component microarrays of biological and biologically active substances. *Anal. Chem.,* 71, 3110-3117.
34. Morozov, V. N., Morozova, T. Ya. (2002) Electrospraying for mass fabrication of chips and libraries. U.S. Pat. No. 63,350,609, Feb. 26, 2002.
35. Myszka, D. G., He, X., Dembo, M., Morton, T. A., Goldstein, B. (1998) Extending range of the rate constants available from BIAcore: interpreting mass transport-influenced binding data. *Biophys. J.* 79, 583-594.
36. Nieba, L., Krebber, A., Pluckthun, A. (1996) Competition BIAcore for measuring true affinities: large differences from values determined from binding kinetics. *Anal. Biochem.* 234, 155-165.
37. O'Neil M. E. *Chem. Eng. Sci.* 23, 1293 (1968)
38. Nuzzo, R. G., Smolinsky, G. Preparation and characterization of functionalized polyethylene surfaces. *Macromolecules.* 17, 1013-1019 (1984).
39. Okun, V. M., Ronacher, B., Blaas, D., Kenndler, E. (1999) Analysis of common cold virus (human rhinovirus serotype 2) by capillary zone electrophoresis. *Anal. Chem.,* 71, 2028.
40. Piehler, J., Brecht, A., Valiokas, R., Liedberg, B., Gauglitz, G. (2000) A high-density poly(ethylene glycole) polymer brush for immobilization on glass-type surfaces. *Biosensors & Bioelectronics,* 15 473-481.
41. Piper, J. W., Swerlick R. A., Zhu. C. (1998) Determining force dependence of two-dimensional receptor-ligand binding affinity. *Biophys. J.,* 74, 492-513
42. Richardson, J., Hawkins, P., Luxton, R. (2001) The use of coated paramagnetic particles as a physical label in a magneto-immunoassay. *Biosensors & Bioelectronics,* 16, 989-993.
43. Schwesinger F., Ros, R., Strunz, T., Anselmetti, D., Guntherodt, H. J., Honegger, A., Jermutus, L., Tiefenauer, L., Pluckthun, A. (2000) Unbinding forces of single antibody-antigen complexes correlate with their thermal dissociation rates. *Proc. Natl. Acad. Sci. USA,* 97, 9972-9977
44. Sheth, S. R., Leckband, D. (1997) Measurements of attractive forces between proteins and end-grafted poly (ethylene glycol). *Proc. Natl. Acad. Sci. USA* 94, 8399-8404.
45. Sofia, S. J., Premnath, V., Merrill, E. W. (1998) Poly (ethylene oxide) grafted to silicon surfaces: grafting density and protein adsorption. *Macromolecules* 31, 5059-5070.
46. Stannard, C. J., Patel, P. D., Haines, S. D., Gibbs, P. A. 1987 Magnetic enzyme immunoassay (MEIA) for staphylococcal enterotoxin B. In: J. M. Grange, A. Fox and N. L. Morgan (Eds.) *Immunological Techniques in Microbiology, Technical Series* no. 24, The Society of Applied Bacteriology, Blackwell Sci. Publ. Oxford.

47. Tunitzkii, N. N. (1970) *Diffusion and Random Processes*, p. 116. Nauka, Novosibirsk.
48. Wong, J., Chilkoti, A., Moy, V. T. (1999) Direct force measurements of the streptavidin-biotin interactions. *Biomolecular Engineering*, 16, 45-55.
49. Wong, J., Kuhl, T. L., Israelashvili, J. N., Mullah, N., Zalipsky, S. (1997) Direct measurement of tethered ligand-receptor interaction potential. *Science*, 275, 820-822.

Although the invention has been described with reference to the above example, it will be understood that modifications and variations are encompassed within the spirit and scope of the invention. Accordingly, the invention is limited only by the following claims.

What is claimed is:

1. A method for detecting analytes comprising:
   a. immobilizing first probe molecules onto a surface of a first semi-permeable membrane that is positioned across a plurality of isolated channels formed from wells of a microplate, wherein only edges of the first semi-permeable membrane are bound to a first support;
   b. placing a second semi-permeable membrane in a position that is parallel to the first semi-permeable membrane, forming a plurality of isolated gaps with the first semi-permeable membrane,
      i. wherein the first probe molecules are inside the gap and facing the second semi-permeable membrane; and
      ii. wherein only edges of the second semi-permeable membrane are bound to a second support;
   c. contacting the side of the first semi-permeable membrane that is outside the gap with a first electrolyte solution, the first electrolyte solution being in contact with a first electrode;
   d. contacting the side of the second semi-permeable membrane that is outside the gap with a second electrolyte solution, the second electrolyte solution being in contact with a second electrode;
   e. filling at least one of the plurality of gaps with an analyte solution or suspension to create a fluid connection between analytes in the analyte solution or the suspension with the first probe molecules;
   f. applying an electric potential to the first electrode and the second electrode to electrophoretically move the analytes toward the first probe molecules;
   g. removing the analytes that are unbound or weakly bound to the first probe molecules; and
   h. detecting analytes bound to the first probe molecules.

2. The method according to claim 1, further including introducing a suspension of particles immobilized with second probe molecules into the analyte solution or the suspension to detect the analytes bound to the first probe molecules.

3. The method according to claim 2, wherein the particles are magnetic particles.

4. The method according to claim 3, wherein the particles are the magnetic particles, further including applying a magnetic field to move the magnetic particles towards the first semi-permeable membrane, allowing the second probe molecules to bind with the analytes that are bound to the first probe molecules.

5. The method according to claim 4, further including reversing the magnetic field to move unbound or weakly bound magnetic particles.

6. The method according to claim 5, wherein the detecting is performed by detecting bound magnetic particles.

7. The method according to claim 3, wherein the particles are the magnetic particles, further including applying an uneven localized magnetic field to direct the magnetic particles towards the first semi-permeable membrane, allowing the magnetic particles to stack over an area of the first semi-permeable membrane.

8. The method according to claim 7, wherein the detecting is performed by moving the stack with the uneven localized magnetic field, allowing the second probe molecules to bind with the analytes that are bound to the first probe molecules.

9. The method according to claim 3, further including applying an uneven magnetic field to direct the magnetic particles towards the first semi-permeable membrane, allowing the magnetic particles to contact the surface of the first semi-permeable membrane and be pushed over the surface by flow while remaining in contact with the surface.

10. The method according to claim 9, wherein the detecting is performed by monitoring where the magnetic beads are arrested.

11. The method according to claim 3, wherein the particles are moved using centrifugal forces.

12. The method according to claim 1, wherein the surface of the first semi-permeable membrane is exposed and activated by plasma prior to the immobilizing and is penetrable for salt and buffer ions, but not for analytes.

13. The method according to claim 12, wherein the surface layer is activated by hydrophobization.

14. The method according to claim 12, wherein at least the first support is activated by plasma.

15. The method according to claim 14, wherein the activation of the surface and the at least first support are activated by plasma simultaneously.

16. The method according to claim 1, wherein the analyte solution is automatically stabilized against convection due to membrane polarization, resulting in a self-forming density gradient.

17. The method according to claim 1, comprising a multitude of the first semi-permeable membrane and a multitude of the second semi-permeable membrane in parallel.

18. The method according to claim 1, further including deflecting bubbles with a frame having a porous membrane.

19. The method according to claim 18, wherein the frame is placed at an angle of at about 30° to about 50° relative to the microplate.

20. The method according to claim 1, wherein:
   i. glue is used to bind the first semi-permeable membrane to the first support and to bind the second semi-permeable membrane to the second support; and
   ii. glue vapor is removed by directing a flow of air through each of the plurality of channels.

21. The method according to claim 20, wherein the glue is cyanoacrylate glue.

22. The method according to claim 21, wherein the glue is octylcyanoacrylate glue.

23. A method for detecting analytes comprising:
   a. immobilizing first probe molecules onto a surface of a first semi-permeable membrane attached to the bottom of wells of a microplate and adjacent a plurality of channels formed from the wells;
   b. placing a second semi-permeable membrane in a position that is parallel to the first semi-permeable membrane, forming a gap with the first semi-permeable membrane, wherein the first probe molecules are inside the gap and facing the second semi-permeable membrane; and
   c. contacting the side of the first semi-permeable membrane that is outside the gap with a first electrolyte solution, the first electrolyte solution being in contact with a first electrode;

d. contacting the side of the second semi-permeable membrane that is outside the gap with a second electrolyte solution, the second electrolyte solution being in contact with a second electrode;

e. filling the gap with an analyte solution or suspension to create a fluid connection between analytes in the analyte solution or the suspension with the first probe molecules;

f. applying an electric potential to the first electrode and the second electrode to electrophoretically move the analytes toward the first probe molecules; and g. detecting analytes bound to the first probe molecules.

24. The method according to claim 23, comprising a plurality of isolated channels and a plurality of isolated gaps.

25. The method according to claim 23, wherein the surface of the first semi-permeable membrane is exposed and activated by plasma prior to the immobilizing and is penetrable for salt and buffer ions, but not for analytes.

26. The method according to claim 23, wherein the analyte solution is automatically stabilized against convection due to membrane polarization, resulting in a self-forming density gradient.

27. The method according to claim 23, wherein:
i. glue is used to bind the first semi-permeable membrane to the first support and to bind the second semi-permeable membrane to the second support; and
ii. glue vapor is removed by providing air through each of the plurality of channels.

* * * * *